US006245968B1

(12) United States Patent
Boudec et al.

(10) Patent No.: US 6,245,968 B1
(45) Date of Patent: Jun. 12, 2001

(54) MUTATED HYDROXYPHENYLPYRUVATE DIOXYGENASE, DNA SEQUENCE AND ISOLATION OF PLANTS WHICH CONTAIN SUCH A GENE AND WHICH ARE TOLERANT TO HERBICIDES

(75) Inventors: Philippe Boudec; Matthew Rodgers, both of Lyons; Florence Dumas, Fleurieu sur Saone; Alain Sailland, Lyons; Hélène Bourdon, Ecully, all of (FR)

(73) Assignee: Aventis CropScience S.A., Lyons (FR)

( * ) Notice: Subject to any disclaimer, the term of this patent is extended or adjusted under 35 U.S.C. 154(b) by 0 days.

(21) Appl. No.: 09/252,292

(22) Filed: Feb. 18, 1999

Related U.S. Application Data

(63) Continuation-in-part of application No. 08/982,772, filed on Dec. 2, 1997, now abandoned.

(30) Foreign Application Priority Data

Nov. 7, 1997 (FR) .................................................. 97 14264

(51) Int. Cl.$^7$ ........................... C12N 15/11; C12N 15/29; C12N 15/83; A01H 5/00; A01H 5/10
(52) U.S. Cl. ..................... 800/278; 435/320.1; 435/410; 435/418; 435/468; 435/471; 536/23.1; 536/23.6; 536/23.7; 800/300
(58) Field of Search .................................. 435/69.1, 320.1, 435/410, 418, 419, 468, 325, 471, 483, 484, 488, 69.7; 536/23.6, 23.7, 23.1; 800/21, 260, 278, 295, 298, 300

(56) References Cited

FOREIGN PATENT DOCUMENTS

| WO 96/38567 | 12/1996 | (WO) | .............................. C12N/15/53 |
| WO97/27285 | 7/1997 | (WO) | .............................. C12N/1/20 |

OTHER PUBLICATIONS

FEBS Letters, 1996, pp. 269–272 "The C–terminal of rat 4–hydroxyphenylpyruvate . . . Enzyme Activity", Lee et al.
Biochemical Journal, 1997, pp. 761–769, "Subcellular localization and purificaiton . . . corresponding cDNA", Garcia et al.
Journal of Biological Chemistry, 1991, vol. 266, pp. 22364–22369, "Site–directed Mutageneises of a Conserved Region . . . Synthase Active Site", Padgette et al.

*Primary Examiner*—Gary Benzion
*Assistant Examiner*—Ashwin Mehta
(74) *Attorney, Agent, or Firm*—Connolly Bove Lodge & Hutz LLP

(57) ABSTRACT

The present invention relates to a nucleic acid sequence encoding a mutated hydroxyphenylpyruvatedioxygenase (HPPD) which exhibits improved tolerance to HPPD inhibitors, to a chimeric gene which comprises this sequence as the coding sequence, and to its use for isolating or obtaining plants which are resistant to certain herbicides.

29 Claims, 4 Drawing Sheets

```
Mus musculus              ------MTTYNN--KGPKPERG--------------------RFLHFHS
Coccidioides immitis      MAPAADSPTLQ-----PAQPSD-------------LN------QYRGYDH
Mycosphaerella graminicola MAPGALLVTSQNGRTSPLYDSDGYVP---APAALVVGGE---VNYRGYHH
Hordeum vulgare           MPPTPTTPAA-TGAAAAVTPEHARP----HR-MVRFNPRSDRFHTLSFHH
Zea mais                  MPPTPTAAAAGAAVAAASAAEQAAFRLVGHRNFVRFNPRSDRFHTLAFHH
Arabidopsis thaliana      MGHQNAAVSE-NQNHDDGAASSPGFKLVGFSKFVRKNPKSDKFKVKRFHH
Daucus carota             MGKK-QSEAE-ILSSNSSNTSPATFKLVGFNNFVRANPKSDHFAVKRFHH
Streptomyces avermitilis  ----MTQTTHHT----PDTARQADP----------------FPVKGMDA
Pseudomonas fluorescens   -----MADLYEN-------PMG--------------------LMGFEF !                  !
Numerotation P. fluorescens      1                  10

Mus musculus              VTFWVGNAKQAASFYCNKMGFEPLAYRGLETGSREVVSHVIKRGKIVFVL
Coccidioides immitis      VHWYVGNAKQAATYYVTRMGFERVAYRGLETGSKAVASHVVRNGNITFIL
Mycosphaerella graminicola AEWWVGNAKQVAQFYITRMGFEPVAHKGLETGSRFFASHVVQNNGVRFVF
Hordeum vulgare           VEFWCADAASAAGRFAFALGAPLAARSDLSTGNSAHASQLLRSGSLAFLF
Zea mais                  VELWCADAASAAGRFSFGLGAPLAARSDLSTGNSAHASLLLRSGSLSFLF
Arabidopsis thaliana      IEFWCGDATNVARRFSWGLGMRFSAKSDLSTGNMVHASYLLTSGDLRFLF
Daucus carota             IEFWCGDATNTSRRFSWGLGMPLVAKSDLSTGNSVHASYLVRSANLSFVF
Streptomyces avermitilis  VVFAVGNAKQAA-HYSTAFGMQLVAYSGPENGSRETASYVLTNGSARFVL
Pseudomonas fluorescens   ISFASPTPGTLEPIFEIMGFTKVATHR-----SKN--VHLYRQGEINLIL
                               .       :      !     .        :        ::: 
                          !         !         !         !
Numerotation P. fluorescens 20        30        40        50

Mus musculus              CSALN---------PWN--------KEMGDHLVKHGDGVKDIAFEVEDC
Coccidioides immitis      TSPLR-SVEQA---SRFP--EDEALLKEIHAHLERHGDGVKDVAFEVDCV
Mycosphaerella graminicola TSPVRSSARQT---LKAAPLADQARLDEMYDHLDKHGDGVKDVAFEVDDV
Hordeum vulgare           TAPYANGCDAA------TASLPSFSADAARRFSADHGIAVRSVALRVADA
Zea mais                  TAPYAHGADAA------TAALPSFSAAAARRFAADHGLAVRAVALRVADA
Arabidopsis thaliana      TAPYSPSLSAGEIKPTTTASIPSFDHGSCRSFFSSHGLGVRAVAIEVEDA
Daucus carota             TAPYSPSTTTSSGS----AAIPSFSASGFHSFAAKHGLAVRAIALEVADV
Streptomyces avermitilis  TSVIK--P--A---TPWG--------HFLADHVAEHGDGVVDLAIEVPDA
Pseudomonas fluorescens   NNEPN-----------S---------IASYFAAEHGPSVCGMAFRVKDS
                                                        ** .*  .* :*:.*
                          !                   !         !
Numerotation P. fluorescens 60                  70        80

Mus musculus              DHIVQKARERGAKIVREPWVEQDKFGKVKFAVLQTYGDTTHTLVEKINYT
Coccidioides immitis      ESVFSAAVRNGAEVVSDVRTVEDEDGQIKMATIRTYGETTHTLIERSGYR
Mycosphaerella graminicola LAVYENAVANGAESVSSPHTDSCDEGDVISAAIKTYGDTTHTFIQRTTYT
Hordeum vulgare           AEAFRASRRRGARPAFAPVDLGRG---FAFAEVELYGDVVLRFVSHPDGT
Zea mais                  EDAFRASVAAGARPAFGPVDLGRG---FRLAEVELYGDVVLRYVSYPDGA
Arabidopsis thaliana      ESAFSISVANGAIPSSPPIVLNEA---VTIAEVKLYGDVVLRYVSYKAED
Daucus carota             AAAFEASVARGARPASAPVELDDQ---AWLAEVELYGDVVLRFVSFGREE
Streptomyces avermitilis  RAAHAYAIEHGARSVAEPYELKDEHGTVVLAAIATYGKTRHTLVDRTGYD
Pseudomonas fluorescens   QKAYNRALELGAQPIHIDTGPMELN----LPAIKGIGGAPLYLIDRFGEG
                            :   **                         .: * .   :.
                          !         !         !         !         !
Numerotation P. fluorescens 90        100       110       120       130
```

FIG. 1A

```
Mus musculus              G---RFLPGFEAPTYKDTLLPKLPRCNLEIIDHIVGNQPDQEMQSASEWY
Coccidioides immitis      G---GFMPGYRMESNADATSKFLPKVVLERIDHCVGNQDWDEMERVCDYY
Mycosphaerella graminicola G---PFLPGYRSCTTVDSANKFLPPVNLEAIDHCVGNQDWDEMSDACDFY
Hordeum vulgare           D--VPFLPGFEGVTNPDAVD-----YGLTRFDHVVGNVP--ELAPAAAYI
Zea mais                  AG-EPFLPGFEGVASPGAAD-----YGLSRFDHIVGNVP--ELAPAAAYF
Arabidopsis thailiana     TEKSEFLPGFERVEDASSFP-LD--YGIRRLDHAVGNVP--ELGPALTYV
Daucus carota             G---LFLPGFEAVEGTASFPDLD--YGIRRLDHAVGNVT--ELGPVVEYI
Streptomyces avermitilis  G---PYLPGYVAAA---PIVEPPAHRTFQAIDHCVGNVELGRMNEWVGFY
Pseudomonas fluorescens   S--SIYDIDFVYLEGVERNP-VG--AGLKVIDHLTHNVYRGRMVYWANFY
                            :  .:               :  :**  *    .:         :
                            !         !         !         !
Numerotation P. fluorescens 140       150       160       170

Mus musculus              LKNLQFHRFWSVDDTQVHTEYSSLRSIVVTNYEESIKMPINEPAPG-RKK
Coccidioides immitis      EKILGFHRFWSVDDKDICTEFSALKSIVMASPNDIVKMPINEPAKG-KKQ
Mycosphaerella graminicola ERCLGFHRFWSVDDKDICTEFSALKSIVMSSPNQVVKMPINEPAHG-KKK
Hordeum vulgare           AGFTGFHEFAEFTAEDVGTTESGLNSVVLANNSEGVLLPLNEPVHGTKRR
Zea mais                  AGFTGFHEFAEFTTEDVGTAESGLNSMVLANNSENVLLPLNEPVHGTKRR
Arabidopsis thaliana      AGFTGFHQFAEFTADDVGTAESGLNSAVLASNDEMVLLPINEPVHGTKRR
Daucus carota             KGFTGFHEFAEFTAEDVGTLESGLNSVVLANNEEMVLLPLNEPVYGTKRK
Streptomyces avermitilis  NKVMGFTNMKEFVGDDIATEYSALMSKVVADGTLKVKFPINEPALA-KKK
Pseudomonas fluorescens   EKLFNFREARYF---DIKGEYTGLTSKAMSAPDGMIRIPLNEESSK--GA
                             *  .  :.    ::    :.* *  .::    :  :*:**
                            !         !         !         !         !
Numerotation P. fluorescens 180       190       200       210       220

Mus musculus              SQIQEYVDYNGGAGVQHIALKTEDIITAIRHLRER----GTEFLAAP-SS
Coccidioides immitis      SQIEEYVDFYNGAGVQHIALRTNNIIDAITNLKAR----GTEFIKVP-ET
Mycosphaerella graminicola SQIEEYVDFYNGPGVQHIALRTPNIIEAVSNLRSR----GVEFISVP-DT
Hordeum vulgare           SQIQTFLEHHGGPGVQHIAVASSDVLRTLRKMRARSAMGGFDFLPPPLPK
Zea mais                  SQIQTFLDHHGGPGVQHMALASDDVLRTLREMQARSAMGGFEFMAPPTSD
Arabidopsis thaliana      SQIQTYLEHNEGAGLQHLALMSEDIFRTLREMRKRSSIGGFDFMPSPPPT
Daucus carota             SQIQTYLEHNEGAGVQHLALVSEDIFRTLREMRKRSCLGGFEFMPSPPPT
Streptomyces avermitilis  SQIDEYLEFYGGAGVQHIALNTGDIVETVRTMRAA----GVQFLDTP-DS
Pseudomonas fluorescens   GQIEEFLMQFNGEGIQHVAFLTDDLVKTWDALKKI----GMRFMTAPPDT
                          .**:  ::    *  *:**.*.  :  ::.  ::       * *:  *
                            !         !         !         !         !         !
Numerotation P. fluorescens 230       240       250       260       270

Mus musculus              YYKLLRENLKSAKIQVKESMDVLEELHILVD-YDEKG---YLLQIFTKPM
Coccidioides immitis      YYEDMKIRLKRQGLVLDEDFETLKSLDILID-FDENG---YLLQLFTKHL
Mycosphaerella graminicola YYENMRLRLKAAGMKLEESFDIIQKLNILID-FDEGG---YLLQLFTKPL
Hordeum vulgare           YYEGVRRLAG--DVLSEAQIKECQELGVLVD-RDDQG---VLLQIFTKPV
Zea mais                  YYDGVRRRAG--DVLTEAQIKECQELGVLVD-RDDQG---VLLQIFTKPV
Arabidopsis thaliana      YYQNLKKRVG--DVLSDDQIKECEELGILVD-RDDQG---TLLQIFTKPL
Daucus carota             YYKNLKNRVG--DVLSDEQIKECEDLGILVD-RDDQG---TLLQIFTKPV
Streptomyces avermitilis  YYDTLGEWVG----DTRVPVDTLRELKILAD-RDEDG---YLLQIFTKPV
Pseudomonas fluorescens   YYEMLEGRLP----DHGEPVDQLQARGILLDGSSVEGDKRLLLQIFSETL
                          **. :                    :* *  .: *    ***:*::  :
                            !         !         !         !
Numerotation P. fluorescens 280       290       300       310
```

FIG. 1B

```
Mus musculus              QDRPTLFLEVIQR---------H------NHQGFGAGNFNSLFKAFEE-E
Coccidioides immitis      MDRPTVFIEIIQR---------N------NFSGFGAGNFRALFEAIER-E
Mycosphaerella graminicola MDRPTVFIEIIQR---------N------NFDGFGAGNFKSLFEAIER-E
Hordeum vulgare           GDRPTLFLEMIQRIGCMEKDERGEEYQKGGCGGFGKGNFSELFKSIEDYE
Zea mais                  GDRPTLFLEIIQRIGCMEKDEKGQEYQKGGCGGFGKGNFSQLFKSIEDYE
Arabidopsis thaliana      GDRPTIFIEIIQRVGCMMKDEEGKAYQSGGCGGFGKGNFSELFKSIEEYE
Daucus carota             GDRPTLFIEIIQRVGCMLKDDAGQMYQKGGCGGFGKGNFSELFKSIEEYE
Streptomyces avermitilis  QDRPTVFFEIIER---------H------GSMGFGKGNFKALFEAIER-E
Pseudomonas fluorescens   MG--PVFFEFIQR---------K------GDDGFGEGNFKALFESIER-D
                             .:*:*.*:*                  *** *** **::*   :
                             |                            |         |
Numerotation P. fluorescens  320                         330       340

Mus musculus              QALRGNLTDLEPNGVRSGM
Coccidioides immitis      QALRGTLI-----------
Mycosphaerella graminicola QDLRGNL-----------
Hordeum vulgare           KSLEAKQS---AAVQGS--
Zea mais                  KSLEAKQAAAAAAAQGS--
Arabidopsis thaliana      KTLEAKQLVG---------
Daucus carota             KTLEAKQITGSAAA-----
Streptomyces avermitilis  QEKRGNL------------
Pseudomonas fluorescens   QVRRGVLTAD---------
                          :  ..
                          |
Numerotation P. fluorescens  350
```

FIG. 1C

Seq_1: HPPD de Pseudomonas fluorescens (Bacterie) 357 aa
Seq_2: HPPD de Synechocystis (Cyanobacterie) 339 aa

```
Seq_1 MADLYENPMGL MGFEFIELAS PTPNTLEPIF E.IMGFTKVA THRSKD..VH
Seq_2            MEFDYLHLYV DDYQSAHRCY QRQWGFTCVN KIITDQGITG

Seq_1 LYRQGAINLI LNNEPHSVAS Y..FAAEHGP SVCGMAFRVK DSQKAYKRAL
Seq_2 IYQQGQILLL ISASESSLSR YADYLQKHPP GVGEVAWQVA NWQKIQHQLS

Seq_1 ELGAQPIHIE TGPMELNLPA IKGIGGAPLY LIDRFGEGSS IYDIDFVFLE
Seq_2 EL....Q.IE TTPVIH..PL TKAEGLTFLL WGDVH...HS IYPVRSELNQ

Seq_1 GVDRHPVGAG LKIIDHLTHN VYRGRMAYWA NFYEKLFNFR EIRYFDIKGE
Seq_2 NKTLH..GVG LTTIDHVVLN IAADQFTQAS QWYQQVFGWS VQQSFTVNTP

Seq_1 YTGLTSKAMT APDGMIRIPL NEESSKGAGQ IEEFLMQFNG EGIQHVAFLS
Seq_2 HSGLYSEALA SANGKVQFNL NCPTNN.SSQ IQTFLANNHG AGIQHVAFST

Seq_1 DDLIKTWDHL KSIGMRFMTA PPDTYYEMLE GRLPNHG.EP VGELQARGIL
Seq_2 TSITRTVAHL RERGVNFLKI PTGYYQQQRN SSYFNYASLD WDTLQCLEIL

Seq_1 LDGSSESGDK RLLLQIFSET LMGP..VFFE FIQRKG.DDG FGEGNFKALF
Seq_2 LDDQDNTG.E RLLLQIFSQP CYGVGTLFWE IIERRHRAKG FGQGNFQALY
                                                        *  *

Seq_1 ESIERDQVRR GVLSTD
Seq_2 EAVETLEKQL EVP..
```

MUTATED HYDROXYPHENYLPYRUVATE DIOXYGENASE, DNA SEQUENCE AND ISOLATION OF PLANTS WHICH CONTAIN SUCH A GENE AND WHICH ARE TOLERANT TO HERBICIDES

This is a continuation-in-part application of Ser. No. 08/982,772 (now abandoned), filed on Dec. 2, 1997 now abandoned.

The present invention relates to a nucleic acid sequence encoding a mutated hydroxyphenylpyruvate dioxygenase (HPPD), to a chimeric gene which comprises this sequence as the coding sequence, and to its use for isolating plants which are resistant to certain herbicides. The invention further relates to plants which contain the nucleic acid of the invention and which may be herbicide resistant, and to methods of growing these plants.

BACKGROUND OF THE INVENTION

The hydroxyphenylpyruvate dioxygenases are enzymes which catalyse the reaction in which para-hydroxyphenylpyruvate (HPP) is transformed into homogentisate. This reaction takes place in the presence of iron (Fe2+) and in the presence of oxygen (Crouch, N. P. et al., Tetrahedron, 53, 20, 6993–7010, 1997). It may be hypothesized that the HPPDs contain an active site which is capable of catalysing this reaction, in which iron, the substrate and the molecule of oxygen link together, although such an active site has not so far been described.

Some molecules which inhibit this enzyme, and which bind to the enzyme in order to inhibit transformation of the HPP into homogentisate, are also known. Some of these molecules have been used as herbicides since inhibition of the reaction in plants leads to whitening of the leaves of the treated plants and to the death of the said plants (Pallett, K. E. et al. 1997 Pestic. Sci. 50 83–84). The herbicides for which HPPD is the target, and which are described in the state of the art, are, in particular, isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-SO2CH3-4-2,3Cl2phenyl)propane-1,3-dione, triketones (EP625505, EP625508, U.S. Pat. No. 5,506,195), in particular sulcotrione, or else pyrazolinates.

Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. etal., J.Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor.

It is this third strategy which was described for successfully obtaining plants which were tolerant to HPPD inhibitors (WO96/38567), with it being understood that this was the first time that a strategy of simply overexpressing the (non-mutated) sensitive target enzyme was successfully used for conferring on plants agricultural level tolerance to a herbicide.

Despite the success obtained with this strategy of simply overexpressing the target enzyme, it is still necessary to improve the system of tolerance to HPPD inhibitors in order to obtain a tolerance whatever the conditions under which the tolerant plants are cultivated, or the commercial doses at which the herbicides are applied in the fields, may be.

BRIEF DESCRIPTION OF THE FIGURES

FIG. 1 shows the alignment of HPPD sequences against a Pseudomonas HPPD sequence (SEQ ID NO:31) as reference. Numbering of the amino acids of the Pseudomonas sequence is provided. Amino acids which are common to the sequences are designated by an asterisk. The HPPD sequences compared to Pseudomonas HPPD are: *Streptomyces avermitilis* (SEQ ID NO:30) (Genebank SAV11864); *Daucus carota* (SEQ ID NO:29) (Genebank DCU87257); *Arabidopsis thaliana* (SEQ ID NO:28) (Genebank AF047834); *Zea mais* (SEQ ID NO:27); *Hordeum vulgare* (SEQ ID NO:26) (Genebank HVAJ693); *Mycosphaerella graminicola* (SEQ ID NO:25) (Genebank AF038152); *Coccicoides immitis* (SEQ ID NO:24) (Genebank COITRP) and *Mus musculus* (SEQ ID NO:23) (Genebank MU54HD).

FIG. 2 shows alignment of the protein sequences of *Pseudomonas fluorescens* HPPD and Synechocystis HPPD. Glycines 334 and 336 of the Pseudomonas HPPD (indicated by stars in the figure) are in positions 318 and 320 in the Synechocystis HPPD.

The present invention therefore relates, first and foremost, to a mutated HPPD which, while being functional, that is to say while retaining its properties of catalysing the transformation of HPP into homogentisate, is less sensitive to HPPD inhibitors than is the native HPPD before mutation.

BRIEF DESCRIPTION OF THE INVENTION

In view of the competitive character of the inhibition, it may be hypothesized that the HPPD inhibitors bind to the enzyme in its active site, or in the vicinity of this active site, so as to block access of the HPP to this active site and prevent its transformation in the presence of iron and water. By effecting a mutation which limits the access of the inhibitor to the active site of the enzyme, while at the same time safeguarding access of the HPP to the active site, it is possible to obtain functional mutated enzymes which are less sensitive to HPPD inhibitors.

It was then observed that, by mutating the enzyme in its C-terminal part, it was possible to obtain functional (enzymatically active) HPPDs which were less sensitive to HPPD inhibitors, such that expression of these functional HPPDs in plants improves the tolerance of the plants to HPPD inhibitors. A number of mutant sequences having these properties are described in this disclosure, and other mutant sequences can be produced using the methods described herein and techniques known in the art. Mutants which are enzymatically active or functional retain a significant portion of HPPD catalytic activity, and in the case of plants transformed with the sequences, the mutated sequences should preferably retain sufficient HPPD activity to sustain the growth of the plant.

The present invention therefore relates to a novel functional mutated HPPD which is less sensitive to HPPD inhibitors and which contains at least one mutation in its C-terminal part.

Referring to the amino acid sequence of HPPD, "mutation" is understood as being the replacement of an amino acid of the primary sequence with another amino acid. The expression "mutated amino acid" will be used below to designate the amino acid which is replaced by another amino acid, thereby designating the site of the mutation in the primary sequence of the protein.

Several HPPDs and their primary sequences have been described in the state of the art, in particular the HPPDs of bacteria such as Pseudomonas (Rüetschi etal., Eur.J.Biochem., 205, 459–466, 1992, WO96/38567), of plants such as Arabidopsis (WO96/38567, Genebank AF047834) or of carrot (WO96/38567, Genebank 87257) of Coccicoides (Genebank COITRP) or of mammals such as the mouse or the pig.

By aligning these known sequences, by using the customary means of the art, such as, for example, the method described by Thompson, J. D. et al, CLUSTALW: improving the sensitivity of progressive multiple sequence alignment through sequence weighting, positions-specific gap penalties and weight matrix choice. Nucleic Acids Research, 22; 4673–4680, 1994), and accessing these computer programs for sequence alignment which are accessible via the Internet, for example, the skilled person is able to define the sequence homologies in relation to a reference sequence and find the key amino acids or else define common regions, making it possible, in particular, to define a C-terminal region and an N-terminal region on the basis of this reference sequence.

In the case of the present invention, the reference sequence is the Pseudomonas sequence, with all the definitions and indications of the positions of particular amino acids being made with respect to the primary Pseudomonas HPPD sequence. The attached Figure1 depicts an alignment of several HPPD sequences which are described in the state of the art; these sequences are aligned with respect to the Pseudomonas HPPD sequence as the reference sequence and comprise the HPPD sequences of *Streptomyces avermitilis* (Genebank SAV 11864), of *Daucus carota* (Genebank DCU87257), of *Arabidopsis thaliana* (Genebank AF047834), of *Zea mais*, of *Hordeum vulgare* (Genebank HVAJ693), of *Mycosphaerella graminicola* (Genebank AF038152), of *Coccicoides immitis* (Genebank COITRP) and of *Mus musculus* (Genebank MU54HD). This figure gives the numbering of the amino acids of the Pseudomonas sequence and also the amino acids which are common to these sequences, with these amino acids being designated by an asterisk. On the basis of such an alignment, it is straightforward, from the definition of the Pseudomonas amino acid by its position and its nature, to identify the position of the corresponding amino acid in another HPPD sequence (with the alignment of sequences of different plant, mammalian and bacterial origin demonstrating that this method of alignment, which is well known to a skilled person, can be generalized to any other sequence). An alignment of different HPPD sequences is also described in Patent Application WO97/49816.

The C-terminal part of the HPPDs, which is where the active site of the enzyme is located, differs from its N-terminal part by a linking peptide which ensures the stability of the enzyme and its oligomerization (the Pseudomonas HPPD is a tetramer while the plant HPPDs are dimers). The linking peptide makes it possible to define the N-terminal end of the C-terminal part of the enzyme, with the said peptide being located between amino acids 145 and 157 in the case of Pseudomonas (FIG. 1).

The C-terminal part can therefore be defined as consisting of the sequence defined, on the one hand, by the linking peptide and, on the other hand, by the C-terminal end of the enzyme, with the mutation which is effected in the C-terminal part of the HPPD therefore being effected in the region which has thus been defined. Two amino acids, which are in positions 161 and 162 in the case of the Pseudomonas sequence (D=Asp161 and H=His162), will be noted in all sequences shown in the sequence alignment depicted in the attached FIG. 1. With reference to the Pseudomonas HPPD, it is therefore possible to define the linking peptide which represents the N-terminal end of the C-terminal part of the HPPD as being located between approximately 5 and 15 amino acids upstream of the amino acid Asp161.

According to a first embodiment of the invention, the mutation is effected on amino acids being located with reference to the Pseudomonas sequence between positions 290 to 350, more preferably between amino acids amino acids 295 to 345, more preferably at at one of positions 298, 332, 333, 334, 336 or 340.

According to a second embodiment of the invention, the mutation is effected on amino acids which are replaced with amino acids exhibiting greater steric hindrance or else with an ionized or ionizable amino acid. Preferably, the mutation is effected on amino acids which have low steric hindrance. According to the invention, an amino acid of low steric hindrance is understood as being glycine.

Any amino acid which exhibits greater steric hindrance than the replaced amino acid can be employed for the mutation according to the invention. Preferably, the amino acids of the mutation site are replaced with the following amino acids: leucine, isoleucine or tryptophan.

According to the invention, an ionized or ionizable amino acid is understood as being any amino acid which exhibits, in addition to the groups which enter into the peptide bond, an amino, carboxylic acid (COOH) or ammonium or —COO— group. The following amino acids of this nature are preferred: glutamine and glutamic acid.

According to a third embodiment of the invention, the mutation is effected on an amino acid of the C-terminal part which is common to several HPPD sequences, with it being possible to identify these latter by the sequence alignment method.

According to a particular embodiment of the invention, the mutated HPPD contains, in its C-terminal part, the following peptide sequence:

- Gly - Phe - Xaa - Yaa- Xab - Asn - Phe - Yab - Yac - Leu - Phe - in which Xaa and Xab, independently of each other represent glycine (Gly) or an amino acid which exhibits a hindrance which is greater than that of glycine, with it being understood that if either Xaa or Xab represents Gly, the other amino acid is then different from Gly, Yaa represents Ala, Lys or Glu, Yab represents Lys, Ser, Arg or Asn, and Yac represents Ala, Ser, Glu or Gln.

Advantageously, at least one of Xaa and Xab represents Leu, Glu, Trp or Ile.

With reference to the Pseudomonas HPPD sequence, the mutated amino acids are selected from the following amino acids: Pro215, Gly298, Gly332, Phe333, Gly334, Gly336, and Ala340 more preferably the amino acids Pro215, Gly336 and Ala340.

The following preferred examples of mutations may be cited: Pro215Leu, Gly336Glu, Gly336Trp, Gly336Ile, or Ala340Gly.

It is understood that the above-described mutations can be combined in pairs, such as, for example, a double mutation of the amino acids Gly334 and Gly336. The present invention also relates to a nucleic acid sequence which encodes a mutated HPPD as described above. According to the present invention, a "nucleic acid sequence" is understood as being a nucleotide sequence which can be of the DNA or RNA type, preferably of the DNA type, and in particular double-stranded, whether it be of natural or synthetic origin, in particular a DNA sequence in which the codons which encode the mutated HPPD according to the invention will have been optimized in accordance with the host organism in which it is to be expressed.

The sequence which encodes an original unmutated HPPD can be of any origin. In particular, it can be of bacterial origin. Advantageous examples which may be cited are bacteria of the Pseudomonas sp. type, for example *Pseudomonas fluorescens*, or else cyanobacteria of the Synechocystis type. The sequence can also be of plant origin, in particular derived from dicotyledonous plants such as tobacco, Arabidopsis, umbelliferous plants such as *Daucus carotta*, or else monocotyledonous plants such as *Zea mais* or wheat. The coding sequences, and the way of isolating and cloning them, are described in the previously cited references, the contents of which are hereby incorporated by reference.

The mutation can be effected in the nucleic acid sequence which encodes the original unmutated HPPD by any means which is appropriate for replacing, in the said sequence, the codon which encodes the mutated amino acid with the codon which corresponds to the amino acid which is to replace it, with the said codons being widely described in the literature and well known to the skilled person, including the following reference: Methods In Molecular Biology, Vol. 57, In Vitro Mutagenesis Protocols, Edited by Michael K. Trower (Humana Press, Totowa, N.J.).

Mutagenesis can also be done in situ according to the known method described in the literature, including WO 98/54330 and the references cited herein.

Several molecular biological methods can be used to achieve this mutation.

A first method consists in subjecting cell cultures to long-term selection pressure with an inhibitor of the HPPD, in the presence or absence of a mutagenic agent, with the HPPD gene then mutating spontaneously under the effect of this selection pressure and, where appropriate, the mutagenic agent, with the said gene having changed such that it encodes a mutated enzyme which enables HPPD activity to be expressed under conditions under which the unmodified enzyme is partially or totally inhibited. The cells can be plant cells or bacteria and, in this latter case, they can express a native HPPD (of bacterial origin) or an HPPD of another origin (bacterial, fungal, algal or plant) which has been introduced into the bacterium employed for the mutagenesis in an appropriate form which permits expression of this HPPD, with the gene encoding the native HPPD of the said bacterium having preferably been deleted, if it exists. Such methods of transforming bacteria are well known to the skilled person, and are amply described in the literature, as are the methods of mutation (in particular: Sambrook etal., Molecular Cloning: A Laboratory Manual, Second Edition, Cold Spring Harbor Laboratory Press, Cold Spring Harbor, N.Y.).

When the cell is a plant cell which is expressing a native HPPD, the mutated HPPD can be isolated and cloned or else plants can be regenerated from the cell cultures using the customary methods. The resulting plants then express a functional mutated HPPD which is less sensitive to HPPD inhibitors than is the native HPPD. The methods of regeneration are amply described in the literature (including the previously cited references) and well known to the skilled person.

The cells which exhibit a mutated HPPD which is less sensitive to HPPD inhibitors are selected using an appropriate screening aid. In view of the object of the present invention, and the sought-after solution, i.e. an HPPD which is less sensitive to HPPD inhibitors, a screening aid which is simple to implement consists in determining the doses of HPPD inhibitor which fully inhibit the original unmutated HPPD, and which are lethal for the cells which express this unmutated HPPD, in subjecting the cells, after mutation, to this predetermined dose, in isolating the mutated cells which have withstood this lethal dose, and then isolating and cloning the gene which encodes the mutated HPPD.

This process of mutagenesis by cell culture was carried out on a very substantial number of Pseudomonas cells which were expressing their native HPPD (see, in particular, the specific examples described below). In all cases, the mutants which were isolated by the above-defined selection method were mutants which exhibited a mutation in the C-terminal part of the HPPD.

Another method for preparing a mutated nucleic acid sequence according to the invention, and the corresponding protein, consists in carrying out site-directed mutagenesis on one or more amino acids which are selected in advance, for example by identifying the amino acids which are common to several sequences in the C-terminal part, or else by attempting to reproduce, in an HPPD of one specific origin, a mutation which was obtained by random mutagenesis (cell culture) in an HPPD of another origin. The methods for obtaining these site-directed mutations are well known to the skilled person and widely described in the literature (in particular: Directed Mutagenesis: A Practical Approach, 1991, Edited by M. J. McPHERSON, IRL PRESS), or are methods for which it is possible to employ commercial kits (for example the U.S.E. mutagenesis kit from PHARMACIA). In all cases, it is useful, after this site-directed mutagenesis, to employ the same method as employed for the above-described random mutagenesis for selecting mutated HPPDs which are less sensitive than the corresponding unmutated HPPD.

Another method for preparing a mutated nucleic acid sequence according to the invention, and the corresponding protein, consists in carrying out a random mutagenesis of short target DNA sequences via PCR with degenerate oligonucleotides, or by <<doping>> each of the four nucleosides involved in the oligonucleotide preparation with a low level of the other three, as disclosed by F. Kirchhoff & R. C. Desrosiers (Methods In Molecular Biology, Vol. 57, In Vitro Mutagenesis Protocols, Chapter 29, pages 323–333, Edited by Michael K. Trower (Humana Press, Totowa, N.J.)) or C. A. Hutchinson III & al. (Proc. Nat. Acad. Sci. USA, Vol 83, 1986, pages 710–714)

The present invention therefore also relates to methods for preparing a nucleic acid sequence which encodes a mutated HPPD according to the invention.

The invention also relates to the use, in a method for transforming plants, of a nucleic acid sequence which encodes a mutated HPPD according to the invention as a marker gene or as a coding sequence which makes it possible to confer on the plant tolerance to herbicides which are HPPD inhibitors. It is of course understood that this sequence can also be used in combination with (an) other gene marker(s) and/or sequence(s) which encode(s) one or more agricultural properties.

The present invention also relates to a chimeric gene (or expression cassette) which comprises a coding sequence as well as heterologous regulatory elements, in the 5' and 3' positions, which are able to function in a host organism, in particular plant cells or plants, with the coding sequence containing at least one nucleic acid sequence which encodes a mutated HPPD as previously defined.

"Host organism" is understood as being any inferior or superior unicellular or multicellular organism into which the chimeric gene according to the invention can be introduced for the purpose of producing mutated HPPD. These organisms are, in particular, bacteria, for example *E. coli*, yeasts, in particular of the genera Saccharomyces or Kluyveromyces, Pichia, fungi, in particular Aspergillus, a baculovirus or, preferably, plant cells and plants.

"Plant cell" is understood, according to the invention, as being any cell which is derived from a plant and which is able to form undifferentiated tissues, such as calli, differentiated tissues such as embryos, parts of plants, plants or seeds.

"Plant" is understood, according to the invention, as being any differentiated multicellular organism which is capable of photosynthesis, in particular a monocotyledonous or dicotyledonous organism, more especially cultivated plants which are or are not intended for animal or human nutrition, such as maize, wheat, rape, soya bean, rice, sugar cane, beetroot, tobacco, cotton, etc.

The regulatory elements which are required for expressing the nucleic acid sequence which encodes an HPPD are well known to the skilled person and depend on the host organism. They comprise, in particular, promoter sequences, transcription activators and terminator sequences, including start and stop codons. The means and methods for identifying and selecting the regulatory elements are well known to the skilled person and widely described in the literature.

The invention relates, more especially, to the transformation of plants. Any promoter sequence of a gene which is expressed naturally in plants, in particular a promoter which is expressed, in particular, in the leaves of plants, such as so-called constitutive promoters of bacterial, viral or plant origin, such as, for example, a histone promoter as described in application EP0507698, or a promoter of rice actin or of a plant virus gene such as, for example, that of cauliflower mosaic virus (CAMV 19S or 35S), or else so-called light-dependent promoters such as that of a gene for the small subunit of plant ribulose biscarboxylase/oxygenase (RuBisCO), or any known promoter which is suitable, can be used as the promoter regulatory sequence in the plants.

According to the invention, it is also possible to use, in combination with the promoter regulatory sequence, other regulatory sequences which are located between the promoter and the coding sequence, such as transcription activators (enhancers) as, for example, the tobacco mosaic virus (TMV) translation activator which is described in application WO87/07644 or the tobacco etch virus (TEV) activator which is described by Carrington & Freed.

Any corresponding sequence of bacterial origin, such as the nos terminator from *Agrobacterium tumefaciens*, or of plant origin, such as a histone terminator as described in application EP0633317, may be used as the terminator regulatory sequence or as the polyadenylation sequence.

According to one particular embodiment of the invention, a nucleic acid sequence which encodes a transit peptide is employed 5' of the nucleic acid sequence encoding a mutated HPPD, with this transit peptide sequence being arranged between the promoter region and the sequence encoding the mutated HPPD so as to permit expression of a transit peptide/mutated HPPD fusion protein, with the mutated HPPD previously defined. The transit peptide makes it possible to direct the mutated HPPD into the plastids, more especially the chloroplasts, with the fusion protein being cleaved between the transit peptide and the mutated HPPD as it crosses the plastid membrane. The transit peptide may be single, such as an EPSPS transit peptide (described in U.S. Pat. No. 5,188,642) or a transit peptide of a plant ribulose biscarboxylase/oxygenase small subunit (RuBisCO ssu), where appropriate including a few amino acids of the N-terminal part of the mature RuBisCO ssu (EP189707), or else a multiple transit peptide which comprises a first plant transit peptide which is fused to a part of the N-terminal sequence of a mature protein having a plastid location, with this part in turn being fused to a second plant transit peptide as described in patent EP508909, and, more especially, the optimized transit peptide which comprises a transit peptide of the sunflower RuBisCO ssu fused to 22 amino acids of the N-terminal end of the maize RuBisCO ssu, in turn fused to the transit peptide of the maize RuBisCO ssu, as described, with its coding sequence, in patent EP508909.

The present invention also relates to the transit peptide/mutated HPPD fusion protein, with the two elements of this fusion protein being defined above.

The present invention also relates to a cloning and/or expression vector for transforming a host organism, which vector contains at least one chimeric gene as defined above. In addition to the above chimeric gene, this vector contains at least one origin of replication. This vector can consist of a plasmid, a cosmid, a bacteriophage or a virus which has been modified by introducing the chimeric gene according to the invention. Such transformation vectors, which depend on the host organism to be transformed, are well known to the skilled person and widely described in the literature. The transformation vector which is used, in particular, for transforming plant cells or plants is a virus, which can be employed for transforming developed plants and which additionally contains its own replication and expression elements. According to the invention, the vector for transforming plant cells or plants is preferably a plasmid.

The invention relates to a method for transforming host organisms, in particular plant cells, by integrating at least one nucleic acid sequence or one chimeric gene as defined above, with it being possible to obtain the transformation by any appropriate known means, which means are amply described in the specialist literature and, in particular, the references cited in the present application, more especially by using the vector according to the invention.

One series of methods consists in bombarding cells, protoplasts or tissues with particles to which the DNA sequences are attached. Another series of methods consists in using, as the means for transfer into the plant, a chimeric gene which is inserted into an *Agrobacterium tumefaciens* Ti plasmid or an *Agrobacterium rhizogenes* Ri plasmid. Other methods may be used, such as microinjection or electroporation or else direct precipitation using PEG. The skilled person will choose the appropriate method depending on the nature of the host organism, in particular the plant cell or the plant.

The present invention also relates to the host organisms, in particular plant cells or plants, which are transformed and which contain a chimeric gene which comprises a sequence encoding a mutated HPPD as defined above.

The present invention also relates to the plants which contain transformed cells, in particular the plants which are regenerated from the transformed cells. The regeneration is obtained by any appropriate method, with the method depending on the nature of the species, as described, for example, in the above references. The following patents and patent applications may be cited, in particular, with regard to the methods for transforming plant cells and regenerating plants: U.S. Pat. Nos. 4,459,355, 4,536,475, 5,464,763, 5,177,010, 5,187,073, EP267,159, EP604662, EP672752, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442174, EP486233, EP486234, EP539563, EP674725, WO91/02071 and WO95/06128.

The present invention also relates to the transformed plants which are derived by cultivating and/or crossing the above regenerated plants, and to the seeds of the transformed plants.

The transformed plants which can be obtained in accordance with the invention can be of the monocotyledonous type, such as cereals, sugar cane, rice and maize, or of the dicotyledonous type, such as tobacco, soya bean, rape, cotton, beetroot, clover, etc.

The invention also relates to a method for selectively weeding plants, in particular plant crops, with the aid of an HPPD inhibitor, in particular a herbicide as previously defined, which method is characterized in that this herbicide is applied to plants which have been transformed in accordance with the invention, either before sowing the crop, before emergence of the crop or after emergence of the crop.

The present invention also relates to a method for controlling weeds in an area of a field which contains seeds or plants which have been transformed with the chimeric gene according to the invention, which method consists in applying, to the said area of the field, a dose of an HPPD inhibitor herbicide which is toxic for the said weeds, without, however, significantly affecting the seeds or plants which have been transformed with the said chimeric gene according to the invention.

The present invention also relates to a method for cultivating the plants which have been transformed, in accordance with the invention, with a chimeric gene according to the invention, which method consists in planting the seeds of the said transformed plants in an area of a field which is appropriate for cultivating the said plants, in applying, if weeds are present, a dose, which is toxic for the weeds, of a herbicide whose target is the above-defined HPPD to the said area of the said field, without significantly affecting the said transformed seeds or the said transformed plants, and in then harvesting the cultivated plants when they reach the desired stage of maturity and, where appropriate, in separating off the seeds of the harvested plants.

In the above two methods, the herbicide whose target is the HPPD can be applied in accordance with the invention, either before sowing the crop, before the crop emerges or after the crop emerges.

Within the meaning of the present invention, "herbicide" is understood as being a herbicidally active substance on its own or such a substance which is combined with an additive which alters its efficacy, such as, for example, an agent which increases its activity (a synergistic agent) or which limits its activity (a safener). The HPPD inhibitor herbicides are, in particular, as previously defined. It is of course to be understood that, for their application in practice, the above herbicides are combined, in a manner which is known perse, with the formulation adjuvants which are customarily employed in agricultural chemistry.

When the plant which has been transformed in accordance with the invention contains another gene for tolerance towards another herbicide (as, for example, a gene which encodes a mutated or unmutated EPSPS which confers on the plant tolerance to glyphosate), or when the transformed plant is naturally sensitive to another herbicide, the method according to the invention can comprise the simultaneous or chronologically staggered application of an HPPD inhibitor in combination with the said herbicide, for example glyphosate.

The invention also relates to the use of the chimeric gene encoding a mutated HPPD as a marker gene during the "transformation/regeneration" cycle of a plant species and selection on the abovementioned herbicide.

The various aspects of the invention will be better understood with the aid of the experimental examples which follow.

DETAILED DESCRIPTION OF THE INVENTION

All the methods or operations which are described below in these examples are given by way of example and correspond to a choice which is made from among the different methods which are available for arriving at the same result. The majority of the methods for manipulating DNA fragments are described in "Current Protocols in Molecular Biology" Volumes 1 and 2, Ausubel F. M. et al., published by Greene Publishing Associates and Wiley Interscience (1989) or in Molecular cloning, T. Maniatis, E. F. Fritsch, J. Sambrook, 1982. The methods needed to carry out the different embodiments of the invention are known in the art and are described in the scientific literature.

EXAMPLE 1

Colorimetric Test For Screening For Mutants Which Exhibit Tolerance to 2-Cyano-3-cyclopropyl-1-(2-SO2CH3-4-CF3phenyl)propane-1,3-dione pRPC The vector pRPA (described in application WO96/38567), which contains a genomic DNA fragment and the coding region of the gene for HPPD from *Pseudomonas fluorescens* A32, was digested with NcoI, purified and then ligated into the expression vector pKK233-2 (Clontech), which itself was digested with NcoI, the site for which forms a unique cloning site in this vector. The orientation of the gene in the resulting pRPC vector which permitted expression under the control of the trc promoter was verified.

A culture medium of the YT broth type, containing 1% agarose (Gibco BRL ultra pure), 5 mM L-tyrosine (Sigma) and the agent for selecting the above mentioned pRPC vector, is dispensed into a 96-well plate at the rate of 100 ml per well. 10 microliter of a culture of *E.coli* in the exponential phase of growth and harbouring the pRPC vector are dispensed into each well. After 16 hours at 37° C., the wells which only contain the culture medium, or those which have been seeded with an *E. coli* culture harbouring the vector pKK233-2, are translucent whereas the wells which have been seeded with an *E. coli* culture harbouring the vector pRPC are coloured brown.

A series of samples was made up with identical culture medium which contained varying concentrations (0 mM to 14 mM) of 2-cyano-3-cyclopropyl-1-(2-methylsulphonyl-4-trifluoromethylphenyl)propane-1,3-dione (EP 0496631), which was dissolved in water and brought to pH7.5. This molecule is a diketonitrile which is recognized as being an effective inhibitor of HPPD activity (Pallett, K. E. et al., 1997. Pestic. Sci. 50, 83–84). The bacterial culture harbouring vector pRPC is observed to be totally without colour in the presence of a 7 mM concentration of the abovementioned compound.

HPPD mutants which were obtained by site-directed mutagenesis as well as by random mutagenesis were selected by rendering brown the medium containing the 2-cyano-3-cyclopropyl-1-(2-methylsulphonyl-4-trifluoromethylphenyl)propane-1,3-dione at a concentration of 7 mM, as will be demonstrated below.

Similar results were obtained by substituting 2-cyano-3-cyclopropyl-1-(2-methylsulphonyl-4-(methylthio)phenyl)propane-1,3-dione and 2-(2-chloro-3-ethoxy-4-(ethylsulphonyl)benzoyl)-5-methyl-1,3-cyclohexadione (WO93/03009) for 2-cyano-3-cyclopropyl-1-(2-methyl-4-trifluoromethylphenyl)-propane-1,3-dione. The two molecules are in solution in DMSO at final concentrations of 3.5 mM and 7 mM in the culture mediums, respectively.

These results confirm that a test which is based on HPPD activity, whatever the origin of this activity, makes it possible to identify HPPD activities which exhibit tolerance to HPPD activity inhibitors of the isoxazole family as well as of the triketone family.

EXAMPLE 2
Random Mutagenesis of the *Pseudomonas fluorescens* A32 HPPD Gene Using Hydroxylamine The plasmid DNA of an *E.coli* culture harbouring the above-described pRPC vector was extracted using the standard protocol. This DNA was incubated, at 80° C. for one hour, with hydroxylamine, which is a chemical mutagen which brings about the replacement of cytosine with thymidine, using a standard protocol. Methods In Molecular Biology, Vol. 57, In Vitro Mutagenesis Protocols, Edited by Michael K. Trower (Humana Press, Totowa, N.J.). The *E.coli* K12 strain DH10B was transformed with the resulting potentially mutated plasmid DNA. Use of the colorimetric screening test described in Example 1 made it possible, after screening several thousand potentially mutated clones, to identify several colonies which were able to render the medium brown, that is to say able to transform HPP into homogentisate even in the presence of 7 mM 2-cyano-3-cyclopropyl-1-(2-methylsulphonyl-4-trifluoromethylphenyl)propane-1,3-dione After sequencing these various mutants, it became evident that the use of this mutagenesis/ screening method had resulted in the isolation of 4 distinct mutants corresponding to three distinct mutation sites:

First site:
  proline 215 replaced by a leucine, which mutant was designated PfL215
Second site:
  glycine 334 replaced by a serine, which mutant was designated PfS334
  glycine 334 replaced by an aspartic acid, which mutant was designated PfD334
Third site:
  glycine 336 replaced by a serine, which mutant was designated PfS336.

These three mutated sites, resulting in an improved tolerance being obtained compared with unmutated HPPD, are located in the C-terminal domain of the protein.

The clones derived from clone pRP C containing the coding region for the gene of HPPD from *Pseudomonas fluorescens* A32 containing one or more mutations are named pRP C followed by the name of the mutation(s), like for example pRP C PfL215 or pRP C PfS336 (or else simply by the only designation of the mutated amino acid, like for example PfL215 or PfS336, unless there is other indication regarding the origin of the mutated HPPD).

The alteration(s) by means of random mutagenesis can be effected on any protein which has an HPPD-type activity, that is to say which transforms 4-hydroxyphenylpyruvate into homogentisate, and whose coding region is or could be cloned. While the HPPDs which are described in this text are, inter alia, those from *P. fluorescens, Arabidopsis thaliana, Daucus carota, Zea mays* and Synechocystis, it is certainly apparent to the skilled person that all these alterations can be applied to other HPPDs.

EXAMPLE 3
Site-Directed Mutagenesis of the *Pseudomonas fluorescens* A32 HPPD Gene by Means of Sequence Analogy By means of aligning the protein sequences of the HPPDs from *Pseudomonas fluorescens* A32, *Arabidopsis thaliana*, mouse, pig and Coccicoides, it is possible to choose a certain number of the amino acids which are found to be conserved in different sequences and then to mutagenize them and obtain tolerant HPPDs; sequences of other HPPDs, described in the literature, could have been added to the alignment which is presented in FIG. 1.

The alignment of these different sequences shows clearly that one of the best conserved regions is located between the phenylalanine at position 333 and the asparagine at position 337. Not only is this region highly conserved but, in addition, it encompasses the two glycines in positions 334 and 336 which were identified by random mutagenesis (in bold in the sequence alignment and marked with a star). Mutagenesis was carried out on the pRPC vector using the Pharmacia U.S.E. mutagenesis kit. The M oligonucleotides were used for mutagenizing phenylalanine 333, glycine 334, glycine 336 and asparagine 337, and also for mutagenizing the double glycine 334 and glycine 336 mutants, as shown in the schemes below (appended sequence identifiers, SEQ ID NO.1 to 12):

Mutagenesis of PHE333, which is replaced exclusively by Trp

GAAGTTGCCC TCGCCCCACC CATCGTCGCC CTT   Oligo 1

Mutagenesis of PHE333, which is replaced exclusively by LEU & ILE

GAAGTTGCCC TCGCCRAKCC CATCGTCGCC CTT   Oligo 2

Mutagenesis of GLY334, which is replaced exclusively by TRP

CTTGAAGTTG CCCTCCCAAA ACCCATCGTC GCC   Oligo 3

Mutagenesis of GLY334, which is replaced exclusively by ASP

CTTGAAGTTG CCCTCGTCAA ACCCATCGTC GCC   Oligo 4

Mutagenesis of GLY334, which is replaced exclusively by SER

CTTGAAGTTG CCCTCGCTAA ACCCATCGTC GCC   Oligo 5

Mutagenesis of GLY334, which is replaced exclusively by LEU & ILE

CTTGAAGTTG CCCTCRAKAA ACCCATCGTC GCC   Oligo 6

Mutagenesis of GLY336 which is replaced exclusively by ASP

CAGCGCCTTG AAGTTGTCCT CGCCAAACCC ATC   Oligo7

Mutagenesis of GLY336, which is replaced exclusively by GLU

CAGCGCCTTG AAGTTYTCCT CGCCAAACCC ATC   Oligo 8

Mutagenesis of GLY336, which is replaced exclusively by TRP

CAGCGCCTTG AAGTTCCACT CGCCAAACCC ATC    Oligo 9

Mutagenesis of GLY336, which is replaced exclusively by Ile

CAGCGCCTTG AAGTTDACTC GCCAAACCCA TC    Oligo 10

Mutagenesis of GLY334 & GLY336, which are replaced by all the other amino acids, and therefore with the possibility of obtaining a double mutant CGCTTGAAGT TNNNCTCNNN AAACCCATCG TC    Oligo 11

Mutagenesis of ASN337, which is replaced exclusively by LEU & ILE

GAACAGCGCC TTGAARAKGC CCTCGCCAAA CCC Oligo 12

After screening several hundred potential mutants with 2-cyano-3-cyclopropyl-1-(2-methylsulphonyl-4-trifluoromethylhenyl)propane-1,3-dione, 13 mutants, of which 10 were single mutants and 3 were double mutants (see summary table), were identified which exhibited tolerance to the 2-cyano-3-cyclopropyl-1-(2-methylsulphonyl-4-trifluoromethylphenyl)propane -1,3-dione inhibitor in our calorimetric detection test. It is necessary to add that some of the mutants which were identified during the course of these site-directed mutageneses are certainly identical to the mutants which were identified in Example 2 (this is the case for PfS334 and PfD334).

It was also possible to combine mutations, not only in regions closed to each other, like for the double mutations in positions 334 and 336, but also in regions far from each other like for the double mutations in positions 215 and 336, like explained here below.

pRP C PfL215 Delta

The plasmidic DNA of clone pRP C PfL215 was digested with PstI, then ligated. The first PstI cleavage site is located at position Leucine 249, and the last PstI cleavage site being within the multiple cloning site of PKK223.3. The clone pRP C PfL215 Delta obtained contains part of the coding sequence of HPPD PfL215, including the mutation Pro215Leu, but not the C-terminal part nor the genomic part.

pRP C PfL215 W336, pRP C PfL215 E336, pRP C PfL215 I336

The plasmidic DNAs of clones pRP C PfW336, pRP C PfE336 or pRP C PfI336 were digested with MluI and HindIII, the MluI cleavage site being located within the coding sequence of HPPD *P. fluorescens* at position Aspartic acid 254, and the HindIII site being located within the multiple cloning site of PKK233.3. The DNA fragments containing the C-terminal parts of the mutated HPPD and the genomic part were purified and then ligated in the plasmid pRP C PfL215 Delta digested with MluI and HindIII. The three clones obtained are equivalent to the clone pRP C PfL215 comprising the coding sequence of HPPD *P. fluorescens* with a first mutation Pro215Leu from pRP C PfL215 and a second mutation W336, E336 or I336, from the C-terminal part of pRP C PfW336, pRP C PfE336 or pRP C PfI336 respectively.

The mutants which were obtained are identified as follows:

| Single mutants | |
|---|---|
| Phenylalanine333 replaced by tryptophan | designated PfW333 |
| Phenylalanine333 replaced by leucine | designated PfL333 |
| Glycine334 replaced by tryptophan | designated PfW334 |
| Glycine334 replaced by aspartic acid | designated PfD334 |
| Glycine334 replaced by serine | designated PfS334 |
| Glycine334 replaced by proline | designated PfP334 |
| Glycine334 replaced by leucine | designated PfL334 |
| Glycine334 replaced by isoleucine | designated PfI334 |
| Glycine336 replaced by aspartic acid | designated PfD336 |
| Glycine336 replaced by glutamine | designated PfQ336 |
| Glycine336 replaced by glutamic acid | designated PfE336 |
| Glycine336 replaced by tryptophan | designated PfW336 |
| Glycine336 replaced by isoleucine | designated PfI336 |
| Asparagine337 replaced by leucine | designated PfL337 |

Double Mutants

Glycine334 replaced by alanine and Glycine336 replaced by alanine: designated PfA334-A336

Glycine334 replaced by alanine and Glycine336 replaced by arginine: designated PfA334-R336

Glycine334 replaced by serine and Glycine336 replaced by histidine: designated PfS334-H336

Proline 215 replaced by Leucine and Glycine 336 replaced by Tryptophan: designated PfL215-W336

Proline 215 replaced by Leucine and Glycine 336 replaced by Glutamic acid: designated PfL215-E336

Proline 215 replaced by Leucine and Glycine 336 replaced by Isoleucine: designated PfL215-I336.

This result demonstrates that it is possible, by means of mutagenizing the amino acids which are conserved between the protein sequences of different HPPDs and which are located in the C-terminal part of the protein, to obtain HPPDs which exhibit tolerance towards inhibitors of HPPD activity. Any region which is conserved between different HPPD amino acid sequences is therefore a good target for obtaining mutants which are advantageous to analyse in order to determine their tolerance. It is evident that any mutation or multiple mutation which would make it possible to obtain a tolerant HPPD, even if this protein is not exemplified in this text, is part of the subject-matter of the invention.

The result also demonstrates that the C-terminal domain is definitely the favoured target for mutagenizing an HPPD with a view to obtaining good tolerance of the enzyme towards these different inhibitors. Thus, it is very difficult to define a conserved region in the N-terminal domain, which is defined as proceeding from amino acid No. 1 to the linking peptide defined previously in the case of *Pseudomonas fluorescens* A32, or to its equivalents in the case of the HPPDs of other species.

The alteration(s) which is/are carried out by means of site-directed mutagenesis on the basis of information deduced from a sequence alignment can be made to any protein which possesses an HPPD-type activity, that is to say which transforms 4-hydroxyphenylpyruvate into homogentisate and whose coding region is or could be cloned. Although the HPPDs which are described in this text are, inter alia, those from *P.fluorescens, Arabidopsis thaliana, Daucus carota, Zea mays* and Synechocystis, it will certainly be apparent that all these alterations can be applied to the other HPPDs.

EXAMPLE 4

Site-Directed Mutagenesis of the *Pseudomonas fluorescens* A32 HPPD Gene

The results which were obtained by random mutagenesis as described in Example 2, as well as those obtained after aligning the different HPPD sequences, clearly demonstrate that the peptide proceeding from F#333 to F#338 (numbering on the *P. fluorescens* HPPD) is a region of particular interest in terms of mutagenizing in order to obtain tolerance.

In parallel with this information, it was found, by means of analysing the three-dimensional structure of the *Pseudomonas fluorescens* strain A32 enzyme, for example (FIG. 2), that the C-terminal part of the protein monomer contains the catalytic site of the enzyme. It is therefore the amino acids of this C-terminal domain which have first and foremost to be mutagenized in the hope of being able to modify the protein/inhibitor interaction and thereby obtain a more tolerant enzyme.

Point mutations which could lead to a conformational change of the Phe333 to Phe338 hexapeptide, without this peptide being directly mutated, have therefore been sought by analysing the three-dimensional structure of the *P. fluorescens* HPPD protein. The principal idea is that mutation of an amino acid which is rather distant from the active site and which is not conserved can influence the spatial positioning of this Phe333 to Phe338 peptide and therefore induce tolerance to HPPD inhibitors by means of an indirect effect.

Amino acids which are close to this hexapeptide were therefore sought in the structure; a small number of amino acids, such as the aspartic acid at position 287 and the glycine at position 298, meet this criterion [for information, the alpha carbon atom of glycine 334 of the hexapeptide is located 9.61 angstroms from the iron atom which is located in the catalytic site, and the alpha carbon of the glycine at position 298 is 5.75 angstroms from that of the glycine which is located at position 334]. Of the two amino acids, this glycine 298 appeared to be the best candidate, since any mutagenesis would lead to an amino acid which had a larger side chain, and this glycine was replaced by a glutamic acid (whose side chain is negatively charged) with a view to obtaining an alteration which was sufficiently appreciable for the effect to be visible.

Furthermore, when the glycine at position 298 is replaced with a glutamic acid, the side chain of this glutamic acid, which side chain is very bulky, "knocks" against the beta-pleated sheet secondary structure in which the conserved LLQIF motif is located. The phenylalanine 312 of this motif is itself located very close to the iron.

The Gly298 to Glu298 mutation was tested.

This Gly298 to Glu298 mutation was brought about by site-directed mutagenesis (U.S.E. mutagenesis kit, Pharmacia) of the pRPC vector using the oligonucleotide No.13 (appended sequence identifier—SEQ ID NO 13):

GLY298 replaced by glutamic acid

GCCTTCCACG GAAGATTCGT CCAGCAGGAT ACC Oligo 13

This mutant, designated PfE298, causes the screening medium containing 7 mM RPA202248 to turn brown (see summary table).

This confirms that it is possible, knowing the three-dimensional structure of the HPPD, to identify a certain number of mutations which are effective in terms of tolerance towards inhibitors of the HPPD, whether the latter be of bacterial, plant or other origin. Thus, it is possible to model the structure of any HPPD whose protein sequence is available, since the precise structure is known in the case of the *P. fluorescens* HPPD. This modelling will be of particular interest when modelling the C-terminal domain, which domain is that which is best conserved in terms of the primary sequence and, in particular, that which is most promising in terms of tolerance towards inhibitors of HPPD.

The alteration(s), which is/are brought about by site-directed mutagenesis on the basis of information deduced from the three-dimensional structure of a modelled HPPD, or the three-dimensional structure which is determined by analysing crystals obtained in the presence or absence of an inhibitor, can be effected on any protein which has an HPPD-type activity, that is to say which transforms 4-hydroxyphenylpyruvate into homogentisate and whose coding region is or can be cloned. While the HPPDs which are described in the present application are, inter alia, those of *P. fluorescens, Arabidopsis thaliana, Daucus carota, Zea mays* and Synechocystis, it will certainly be apparent to the skilled person that all these alterations can be applied to other HPPDs.

EXAMPLE 5

Random Mutagenesis of the *P. fluorescens* A32 HPPD Gene by <<Doping>> Oligonucletides The nucleotide sequence corresponding to aminoacids 333 to 347 (SEQ ID NO 22) was synthesised by OligoExpress∩ where each recipient containing one of the bases A, T, G or C was containing 97% of the said base and 1% of each of the other bases. A population of oligonucleotides is then created containing either 0, 1, 2 or n mutations in the oligonucleotide sequence compared to the sequence of origin (SEQ ID NO 22). The mutagenesis of the HPPD gene was done using the above <<doped>> nucleotides with the use of the USE Mutagenesis Kit (Pharmacia) following the recommendations on the product. The DNA sequence used for mutagenesis was the HPPD sequence of pRP C as disclosed in example 1. The selection of the mutant was done using the colorimetric method disclosed in example 1. 1200 different colonies were screened, 8 of them showing an important brown colour in presence of the selection agent. The plasmid DNA of these 8 colonies was extracted and sequenced in the area of potential mutations (between amino acids 333 and 347. 6 of the clones were showing the same mutation Ala340Gly.

EXAMPLE 6

Expression of Mutant *Pseudomonas fluorescens* HPPDs in Tobacco

A) Construction of Chimeric Genes pRP-VB3

The DNA of the binary vector pBI121 (Clontech) was digested with HindIII and XbaI and the ends were filled in with dNTPs using pfu polymerase (Stratagene); the vector was purified. The DNA of the clone pRP-S, which is described in Example 2 of the application PCT96/38567 and which comprises the sequence "double histone promoter—TEV—OTP—HPPD gene—Nos terminator" was digested with HindIII and SacI and the ends were filled in with dNTPs using pfu polymerase (Stratagene); the purified insert was then ligated into the previously described purified vector.The orientation was verified by means of SalI digestion. The clone pRP-VB3 therefore has the following chimeric gene structure:

RB/Nos promoter/NPTII/Nos terminator/double histone promoter/tev/otp/HPPD/Nos terminator RB=right-hand border of the *Agrobacterium tumefaciens* T-DNA Nos promoter=promoter of the *Agrobacterium tumefaciens* nopaline synthase NPTII=sequence encoding the type II neomycin phosphotransferase for resistance to kanamycin NOS terminator=terminator sequence of the *Agrobacterium tumefaciens* nopaline synthase Double histone promoter=described in EP507689
tev=TEV enhancer (Carrington & Freed)
otp=optimized transit peptide (EP 508 909)

pRP-VB3-b

The DNA of clone pRP-VB3 was digested with BamHI, purified and then ligated into the vector pZERO-1 (Invitrogen), which does not contain the BstEII and SalI restriction sites and which was digested with BamHI, and the resulting vector was purified. A part of the OTP, the gene for HPPD and the Nos terminator are in this way transferred into pZERO-1.

pRP-VB3-c

The DNA of clone pRP-VB3-b was digested with SalI, purified and then ligated in the presence of the adapter shown below (oligonucleotides 14 and 15—SEQ ID NO 14 and 15 appended) so as to replace the SalI restriction site with the BstEII restriction site.

5'TCGAGAGAGAGGTGACCGAGAGA 3'

3'CTCTCTCCACTGGCTCTCTAGCT 5' pRP-VB3-d

The DNA of clone pRP-VB3-c was digested with BamHI, and the insert was purified and then cloned into the PUC19 vector (Biolabs) which had been digested with BamHI. A part of the OTP, the gene for HPPD and the Nos terminator are in this way transferred into PUC19.

pRP-VB3-e

Since the PUC19 vector does not possess PmlI and StuI restriction sites, the DNA of clone pRP-VB3-d was digested with PmlI and StuI, purified and then ligated to itself, thereby making it possible to delete the Not site in the HPPD gene and to shorten the coding part of the HPPD by approximately 500 base pairs in order subsequently to facilitate screening of the transformed colonies which have integrated the mutant HPPDs.

pRP-V3-f

Vector pRP-VB3-e was digested with NotI and the ends were filled in with dNTPs using pfu polymerase (Stratagene), after which the DNA was purified; it was then digested with BamHI, purified and then cloned into the KpnI-digested PUC19 vector, whose ends had been filled in with dNTPs using pfu polymerase (Stratagene), after which it was purified, digested with BamHI and purified.

pRP-VB83-g

The DNA of clone pRP-VB3 was digested with BstEII and the ends were filled in with dNTPs using pfu polymerase (Stratagene); the purified vector was then ligated to itself thereby making it possible to eliminate the unique BstEII site of this vector.

pRP-RD224

The DNA of clone pRP-VB3-f was digested with BamHI and SacI, purified and then ligated into vector pRP-VB3-g, which had been digested with BamHI and SacI and purified. Clone pRP-RD224 therefore has the following structure:

RB/Nos promoter/NPTII/Nos terminator/double histone promoter/tev/otp/truncated HPPD/Nos terminator/LB LB=left-hand border of the *Agrobacterium tumefaciens* T-DNA pRP-RD224 Mutants The DNAs of the vectors carrying the mutated HPPDs as well as the unmutated HPPD contained in vector PKK233-2 were digested with KpnI and BstEII, purified and then ligated into vector pRP-RD224, which had been digested with KpnI and BstEII and purified. The transformants which had integrated the mutated HPPD gene were selected for the size of the insert by digesting with KpnI and BstEII. The resulting clones are designated pRP-RD224 to which is added the type of mutation which has been carried out on the HPPD; in this way, the following clones were, for example, created: pRP RD224 Pf (for the unmutated enzyme), pRPRD224 PfD336 (for the enzyme having an aspartic acid at position 336), pRPRD224 PfQ336 (for the enzyme having a glutamine at position 336), pRPRD224 PfL333 (for the enzyme having a leucine at position 333) and pRPRD224 PfA334-A336 (for the enzyme having an alanine at position 334 and at position 336, i.e. a double mutant).

B) Transformation of "*Petit havana*" Tobacco

The previously described chimeric genes were transferred into "*Petit havana*" tobacco using the transformation and regeneration procedures which have already been described in European application EPNo.0508909.

1) Transformation

The vector is introduced into the non-oncogenic *Agrobacterium tumefaciens* strain EHA101.

2) Regeneration

The "*Petit havana*" tobacco was regenerated from foliar explants on a basal Murashige and Skoog (MS) medium comprising 30 g/l sucrose as well as 350 mg/l cefotaxime and varying doses, i.e. 10 ppm, 20 ppm and 40 ppm, of 2-cyano-1-[4-(methylsulphonyl)-2-trifluoromethylphenyl]-3-(1-methylcyclopropyl)propane-1,3-dione (EP496630), which is an analogue of 2-cyano-3-cyclopropyl-1-(2-methylsulphonyl-4-trifluoromethylphenyl)propane-1,3-dione, or direct doses of 2 or 4 or 8 ppm of 2-cyano-3-cyclopropyl-1-(2-methylsulphonyl-4-trifluoromethylphenyl)propane-1,3-dione. The foliar explants are removed from greenhouse plants and transformed by the foliar disc technique (Science 1985, Vol.227, p.1229–1231) in three consecutive stages:

the first comprises inducing shoots on an MS medium to which is added 30 g/l sucrose and which contains 0.05 mg/l naphthylacetic acid (ANA) and 2 mg/l benzylaminopurine (BAP) for 15 days and in the presence of varying doses of herbicide, i.e. 2-cyano-1-[4-(methylsulphonyl)-2-trifluoromethylphenyl]-3-(1-methylcyclopropyl)propane-1,3-dione (EP496630) or 2-cyano-3-cyclopropyl-1-(2-methylsulphonyl-4-trifluoromethylphenyl)propane-1,3-dione.

The green shoots which are formed during this stage are then developed by culturing them, for 10 days, on an MS medium to which is added 30 g/l sucrose and which contains varying doses of herbicide but does not contain any hormone.

Developed shoots are then removed and cultured on an MS rooting medium containing half concentrations of salts, vitamins and sugars and varying doses of isoxaflutole but not containing any hormone. After about 15 days, the rooted shoots are placed in soil.

C) Measuring the Tolerance of the Plantlets to Herbicide in vitro

The experiments are carried out by reacting a selective agent with mutants pRPRD224PfL333, pRPRD224PfA334-A336, pRPRD224PfD336 and pRPRD224PfQ336. They demonstrate that while shoots/plantlets are not obtained at the highest doses of herbicide in the transformation/regeneration assays using an unmutated HPPD, the mutants, by contrast, make it possible, due to the tolerance of the enzyme being improved, to obtain plantlets even at high doses of 40ppm of 2-cyano-1-[4-(methylsulphonyl)-2-trifluoromethylphenyl]-3-(1-methylcyclopropyl)propane-1,3-dione (EP496630) or 8 ppm of 2-cyano-3-cyclopropyl-1-

(2-methylsulphonyl-4-trifluoromethylphenyl)propane-1,3-dione. These plantlets, which are obtained at high concentrations of the selective agent when a mutated HPPD is used and which it is not possible to obtain when wild-type HPPD is used, are normal in appearance.

We may add that mutants pRPRD224PfD336 and pRPRD224PfL333 are statistically more efficacious than mutants pRPRD224PfQ336 and pRPRD224PfA334-A336 since they enable a larger number of tolerant plantlets to be obtained.

Table summarizing the mutants of *P. fluorescens* HPPD

| HPPD type | Activity in the screening test* using a selective agent dose of | |
|---|---|---|
| | 0 mM | 7 mM |
| Wild type | 10 | 0 |
| Mutated | | |
| PfL215 | 10 | 7 |
| PfE298 | 8 | 3 |
| PfL333 | 5 | 4 |
| PfW333 | — | — |
| PfS334 | 7 | 7 |
| PfD334 | 1 | 1 |
| PfW334 | 6 | 6 |
| PfP334 | 5 | 5 |
| PfL334 | 5 | 4 |
| PfI334 | 5 | 4 |
| PfS336 | — | — |
| PfD336 | 2 | 1 |
| PfQ336 | 8 | 8 |
| PfE336 | 10 | 8 |
| PfW336 | 10 | 10 |
| PfI336 | 10 | 8 |
| PfL337 | 8 | 8 |
| PfA334-A336 | 8 | 8 |
| PfA334-R336 | 8 | 7 |
| PfS334-H336 | 5 | 5 |

*: screening test described in Example 1.
— data not available.

The number 10 corresponds to a high activity of the same level as that obtained with unmutated HPPD in the absence of inhibitor, while the figure 0 corresponds to no activity, either due to complete inhibition by 2-cyano-3-cyclopropyl-1-(2-methylsulphonyl-4-trifluoromethylphenyl)propane-1,3-dione or due to a mutation which results in the enzyme becoming inactive; the numbers 1 to 9 correspond to intermediate activities, with the activity increasing as the number increases.

These results confirm that introducing an HPPD exhibiting a tolerance to inhibitors of HPPD activity into plants confers a tolerance to these same inhibitors on the plants, which tolerance therefore appears to be superior to that which is obtained with an unmutated HPPD.

C) Tolerance in vivo (Greenhouse)

During the selection in vitro on 2-cyano-3-cyclopropyl-1-(2-methylsulphonyl-4-trifluoromethylphenyl)propane-1,3-dione at 1, 2, 4 and 8 ppm, it is apparent that some of the mutants will not allow an easy regeneration of the tobacco plantlets transformed, at any of the doses used. One should note however that transformants of these mutants may be obtained simply by increasing the numbers of transformation assays.

The mutants leading to the greater numbers of plantlets are PEL215, PfD336 and PfQ336.

With the above mutants, the following numbers of transformation events were obtained for one assay at the different doses of the selection agent 2-cyano-3-cyclopropyl-1-(2-methylsulphonyl-4-trifluoromethylphenyl)propane-1,3-dione:

with PfD336:
  25% of events at 1 ppm
  25% of events at 2 ppm
  35% of events at 4 ppm
  15% of events at 8 ppm with PfL215:
  8% of events at 1 ppm
  60% of events at 2 ppm
  8% of events at 4 ppm
  24% of events at 8 ppm with PfQ336:
  35% of events at 1 ppm
  25% of events at 2 ppm
  40% of events at 4 ppm
  0% of events at 8 ppm with non mutated Pf HPPD:
  15% of events at 1 ppm
  70% of events at 2 ppm
  15% of events at 4 ppm
  0% of events at 8 ppm These results will confirm that mutated HPPD according to the invention are statistically more tolerant to the selection agent than the native unmutated HPPD. With the two mutants PfD336 and PfL215 it is possible to obtain transformants at the highest dose of selection agent, when it is not possible with the native unmutated HPPD.

Moreover, with mutant PfQ336, a great number of mutants are obtained at 4 ppm of selection agent, when a very low percentage of transformats is obtained with the native unmutated HPPD at the same dose of selection agent.

All the plants, are acclimated in greenhouse and grown until seeds.

After harvest, the seeds are planted in soil and treated by preemergence application with isoxaflutole (IFT) at doses of 400 and 600 g/ha. Following the emergence of plants, phytotoxicity measurements are done for the various transformation events. The results show that in the tobacco, genotype Little Havana, the mutated HPPD Pf336 and PfQ336 do have a better tolerance to herbicides inhibiting HPPD (like IFT) than the native unmutated Pf HPPD.

These results also show that the position 336 is important to obtain HPPD with increased tolerance to HPPD inhibitor herbicides, more tolerant that the native unmutated HPPD.

Each plantlets corresponding to distincts transformation events are then transferred to ground and treated, post-emergence, with IFT at doses of 600 g/ha at the 6 leafs stage. The plantlets show marks of bleaching symptoms of the leafs, but all show a tolerance to IFT.

The plants are grown to maturity in greenhouse and the seeds are collected/harvested. The seeds of several flowers are mixed and sown on a mixture of loam and sand, with about 100 seeds for each planting (seedling) box. The genotype Little Havana is included as control. The treatments are done after sowing by spraying IFT at doses of 600 g/ha of IFT. Notations of the aspect of the plantlets are noted 12 days after treatment with the note 5 for the best aspect and the note 1 for the worst. The mean of the note obtained for several transformation events (10 to 20 transformation events per HPPD evaluated) represents the value of tolerance to IFT of mutated and non mutated HPPDs in pre-emergence treatment.

The results obtained for mutated HPPDs at positions 336 and 215 are reported in the Table here below.

| Assay | 1 | 2 |
|---|---|---|
| unmutated Pf (control) | 2.06 | 2.2 |
| PfW336 | — | 2.8 |
| PfD336 | 3.35 | — |
| PfQ336 | 2.94 | — |
| PfL215 | 3 | — |

These results show that in transformed plants, the level of tolerance to HPPD inhibitor herbicides is higher with mutated HPPDs according to the invention than with the corresponding unmutated native HPPD.

The following greenhouse in vivo experiments were further conducted to compare the level of tolerance to IFT of tobacco plants transformed with mutants PfW336, PfE336, PfI336 et PfL215. Evaluation he aspect of the plantlets is noted several days after treatment (DAT) with 5 for the best aspect and 0 when the plantlets are completely destroyed.

Assay 3:
50 g/ha and 600 g/ha IFT preemergence, on loam,
8 transformation events for PfE336, 10 transformation events for PfW336, 6 transformation events for PfI336 and 5 transformation events for PfL215,
50 seeds per transformation event, evaluation 11 DAT.

| | 50 g/ha | 600 g/ha |
|---|---|---|
| HPPD PfE336 | 3 | 2.4 |
| HPPD PfW336 | 3.5 | 3.8 |
| HPPD PfI336 | 2.8 | 2.5 |
| HPPD PfL215 | 4 | 3.2 | low dose L215 > W336 > E336 = I336
high dose W336 > L215 > E336 = I336

Assay 4:
600 g/ha IFT preemergence, on loam,
5 transformation events for Pf (control)
and PfL215, 10 PfW336, 50 seeds per event.

| | 9 DAT | 19 DAT |
|---|---|---|
| HPPD PfW336 | 2.3 | 3.6 |
| HPPD PfL215 | 2.6 | 1.2 |
| HPPD Pf | 2 | 1.6 |

9 DAT L215 > W336 > HPPD Pf
19 DAT W336 >> HPPD Pf = L215

Assay 5:
600 g/ha IFT preemergence, on loam,
5 transformation events for HPPD,
50 seeds per event.

| | 11 DAT | 21 DAT |
|---|---|---|
| HPPD PfW336 | 2.4 | 4 |
| HPPD PfL215 | 2.2 | 2 |
| HPPD PfW336 | 2.5 | 3.5 |
| HPPD Pf (control) | 1 | 1 |

11 DAT W336 >= L215 > HPPD Pf
21 DAT W336 >> L215 > HPPD Pf

Assay 6:
100, 200, 300 and 400 g/ha IFT preemergence,
on vermiculite, 2 transformation events for PfW336
1 transformation event for the other, 100 seeds per
transformation event, 2 repeated trials.

| | 100 g/ha | 200 g/ha | 300 g/ha | 400 g/ha |
|---|---|---|---|---|
| 7 DAT | | | | |
| HPPD PfW336 | 2.5 | 2 | 2.5 | 3 |
| HPPD PfW336 | 2.5 | 2 | 2.5 | 2.5 |
| HPPD PfL215 | 2.5 | 3 | 3 | 3 |
| HPPD PfQ336 | 2 | 2.5 | 2 | 2 |
| HPPD Pf | 1 | 1 | 1 | 1 |
| W336 = L215 > Q336 > HPPD Pf | | | | |
| 15 DAT | | | | |
| HPPD PfW336 | 2 | 1.5 | 0 | 0 |
| HPPD PfW336 | 2 | 1.5 | 0 | 0 |
| HPPD PfL215 | 1.5 | 0 | 0 | 0 |
| HPPD PfQ336 | 0 | 0 | 0 | 0 |
| HPPD Pf | 0.5 | 0 | 0 | 0 |

W336 > L215 > Q336 = HPPD Pf

EXAMPLE 7
Site-Directed Mutagenesis of the Synechocystis HPPD Gene

A mutation site which is effective in terms of tolerance to HPPD inhibitors is chosen in the *Pseudomonas fluorescens* HPPD and the site is transposed to another HPPD.

This transposition is made to an HPPD which is as different as possible from the HPPD of *Pseudomonas fluorescens* and from other known HPPDs. The gene which was chosen for this work was the gene encoding Synechocystis HPPD, which gene was known due to the systematic sequencing of the genome of this cyanobacterium but had never been cloned as such. The gene was therefore first of all isolated and then expressed in *E. coli*.

1) Isolation of the Gene

The genomic DNA of the cyanobacterium Synechocystis PCC6803 was extracted and purified using the standard protocols. 200 mg of this genomic DNA were amplified by polymerization chain reaction (PCR) using 1.25 U of pow polymerase (Boehringer) in its buffer, in a reaction volume of 50 ml containing 200 mM of dNTP (deoxyribonucleotide triphosphate). The synthetic oligonucleotide sequences 16 and 17 (SEQ ID NO 16 and 17), which were used as primers were deduced from the sequence of Synechocystis HPPD which was published in Genebank.

ATTATGGAAT TCGACTATCT T          Oligo 16

CAGTATTCAT AATGTTAATT ATG        Oligo 17

The amplification program, i.e. 5 minutes at 94° C., then 50 cycles of 1 minute at 94° C., 1 minute at 49° C. and 1 minute at 72° C., then 5 minutes at 72° C., was Perkin-Elmer 9600 apparatus.

2) Cloning and Expression of the Gene

The amplified fragment which was obtained by PCR was purified, digested with EcoRI, repurified and then cloned into the vector ptrc-99 A (Pharmacia), which had previously been digested with EcoRI and SmaI. The bacterium JM105 was transformed with the recombinant plasmid. The conformity of the cloned fragment with the published Synechocystis HPPD sequence was verified by sequencing.

The dioxygenase activity of the Synechocystis HPPD which had thus been obtained was observed by the browning of the medium, using the previously described colorimetric test, with addition of IPTG (isopropyl-b-D-thiogalactopyranoside) at a concentration of 1 mM in order to induce expression of the protein. Under the same conditions, but in a medium containing 7 mM 2-cyano-3-cyclopropyl-1-(2-methylsulphonyl-4-trifluoromethylphenyl)propane-1,3-dione, there is no browning of the medium, thereby confirming inhibition of the Synechocystis HPPD activity by the 2-cyano-3-cyclopropyl-1-(2-methylsulphonyl-4-trifluoromethylphenyl)propane-1,3-dione.

3) Site-Directed Mutagenesis

By means of aligning the protein sequences of the *Pseudomonas fluorescens* A32 HPPD and of the Synechocystis PCC6803 HPPD, it was estimated that the glycines in positions 334 and 336 of the Pseudomonas HPPD (glycines which are indicated by stars in FIG. 2 and which are highly conserved) are in positions 318 and 320 in the Synechocystis HPPD.

With several mutants at position 334 in *Pseudomonas fluorescens* having been obtained, two site-directed mutagenesis experiments (U.S.E., Pharmacia) were carried out using the oligonucleotides MUGLYA and MUGLYB, which oligonucleotides were intended to replace the glycine at position 318 (of Synechocystis corresponding to the glycine at position 334 of *P.fluorescens*) either with an asparagine or a serine or with a proline or an alanine (SEQ ID NO 18 and 19).

GLY318, possible replacement with SER & ASN

CGGGCAAAAG GATTTARCCA AGGAAACTTT
CAAG                                                      Oligo 18

GLY318, possible replacement with PRO & ALA

CGGGCAAAAG GATTTSCNCA AGGAAACTTT
CAAG                                                      Oligo 19

In the two experiments, clones obtained after mutagenesis caused browning of the screening medium at 7 mM 2-cyano-3-cyclopropyl-1-(2-methylsulphonyl-4-trifluoromethylphenyl)propane-1,3-dione (test described in Example 1). One mutant from each experiment was sequenced.

Glycine318, replaced with asparagine, designated SyN318, similar to PfD334 (in Example 3).

Glycine318, replaced with alanine, designated SyA318, similar to PfA334 (in Example 3).

These results confirm that mutations leading to tolerance, which tolerance is demonstrated for a given HPPD, are transposable to another HPPD which belongs to another species and another kingdom.

These results also confirm that alterations of the protein sequence in the C-terminal part of an HPPD can, whatever the origin of the HPPD (bacterial or other origin) result in tolerance towards HPPD inhibitors

EXAMPLE 8

Biochemical Study of a Mutated HPPD; Mtants of Synechocystis

The mutants SyN318 and SyA318 which were obtained in the previous example were examined, in comparison with the unmutated HPPD of Synechocystis, for the biochemical characteristics Km and IC50 with regard to an HPPD inhibitor, i.e. 2-cyano-3-cyclopropyl-1-(2-methylsulphonyl-4-trifluoromethylphenyl)propane-1,3-dione. This analysis was carried out using the following protocol:

a) Measuring Activity

The HPPD activity is measured by determining, by means of high performance liquid chromatography (HPLC), the quantity of product, i.e. homogentisate, which is formed after incubating the enzyme with its substrate HPP. Injecting different amounts of homogentisate, varying from 12 to 48 nmoles, into the column enables the retention time of the homogentisate to be determined and the peak area to be correlated with the quantity of product injected.

The activity measurements are carried out in a final volume of 200 ml containing: 12.6 mM ascorbate, 178 mM iron (FeH8N2O8S2,6H2O) (previously prepared in 0.1 M tris-acetate buffer, pH6), 50 mg of crude extract containing the HPPD, 352 mM HPP and 0.1 M tris-acetate buffer, pH7.5. The enzyme is firstly incubated with the iron at 30° C. for 1 min and then with the ascorbate at 30° C. for 5 min before the reaction is started by adding the substrate, i.e. the HPP. The incubation is continued at 30° C. for 1 min 30sec and the reaction is then stopped by adding 70 ml of 20% perchloric acid. The proteins are then removed by centrifuging for 5min at 15,300 rpm and at 20° C. The supernatant is recovered. The quantity of homogentisate formed is then analysed by injecting 75 ml of assay mixture into a Pico TagC18 column which is connected to the HPLC system. Elution is carried out at a flow rate of 1 ml/min. The isocratic elution which is carried out is as follows: 1—0% of buffer B (that is 100% of bufferA: water, 3% (v/v) acetonitrile, 0.1% (v/v) trifluoroacetic acid) for 6 minutes; 2—100% of buffer B (100% acetonitrile) up to the 11th minute; 3—0% of buffer B up to the 19$^{th}$ minute. On leaving the column, the homogentisate is detected by measuring absorbance at 288 nm. The quantity of product formed is defined by the area of the peak on the chromatogram.

b) Determination of the Km

The Km of the HPPD for HPP is determined by measuring the initial velocity of the reaction using different concentrations of HPP. The reactions are carried out under the above-described conditions using HPP concentrations of from 5.5 mM to 1400 mM.

c) Determination of the IC50

The IC50 is determined by measuring the initial velocity of the reaction under the above-described conditions after incubating the enzyme at 30° C. for 10 min with the iron, the ascorbate, the substrate at a concentration of 1056 mM and varying concentrations of inhibitor. The concentrations of 2-cyano-3-cyclopropyl-1-(2-methylsulphonyl-4-trifluoromethylphenyl)propane-1,3-dione employed vary from 10-10 to 10-4 M.

The Km values of the enzyme for its substrate, i.e. 4-hydroxyphenylpyruvate, which were calculated, and the IC50 values which were calculated at comparable activities, are recorded in the table below:

|  | Native HPPD | SyN318 | SyA318 |
| --- | --- | --- | --- |
| Km | 60 mM | 470 mM | 320 mM |
| IC50 | 80 nM | 80 mM | 40 mM |

These results confirm that while the mutations which are carried out in the C-terminal part of the protein exert an influence by diminishing the affinity of the enzyme for the substrate (Km), they exert an even stronger influence by diminishing the affinity of the enzyme for the inhibitor (IC50). Thus, the ratio of the IC50 of a mutant HPPD to the IC50 of the non-mutant HPPD (which reflects the loss of affinity for the inhibitor) is 1000 and 500 for SyN 318 and SyA 318, respectively, while the ratio of the Km of a mutant HPPD to the Km of the non-mutant HPPD (which reflects the loss of affinity for the substrate) is 8 and 5 for SyN 318 and SyA 318, respectively. This illustrates very well the fact that, while these two mutants have a slightly lower affinity for the substrate of the enzyme, they in particular have a markedly lower affinity for inhibitors of the enzyme, including 2-cyano-3-cyclopropyl-1-(2-methylsulphonyl-4-trifluoromethylphenyl)propane-1,3-dione.

These results confirm that the colorimetric screening test described in Example 1 does indeed make it possible to detect mutated HPPDs which exhibit tolerance to inhibitors of HPPD activity. They validate the method which is being used to screen and identify HPPD mutants which are tolerant towards inhibitors of HPPD. While this screening method is rapid and simple to use, and this is why it is being employed, it is clear that any other method can be used in order to make a similar analysis; it would be possible to use
- a screening method which measures activity, and its inhibition, and which is based on the disappearance of HPP (radioactive assay, spectrophotometric assay or other assay) or based on the consumption of oxygen or based on the appearance of homogentisate (with coupling to another enzyme activity)
- an in vivo screening method, such as the growth of bacteria on HPP as the sole carbon source in the presence of inhibitors of HPPD, thereby making it possible to select the only clones having a tolerant HPPD
- it is similarly entirely possible to envisage using an in vivo screening in plants by employing plant transformation vectors, transformation systems, regeneration systems and selection systems with an inhibitor of HPPD, such as those described in Examples 5 and 8.

EXAMPLE 9

Evaluation of the Unmutated and Mutated HPPD of Synechocystis; SyN318 and Mutated SyA318 in Tobacco A) Construction of the Chimeric Genes The vector which is employed in order to make the construct which enables Synechocystis HPPD (wild-type or mutant) to be expressed in type PBD6 tobacco plants is designated pRD224 (described in Example 5). This vector was initially conceived for cloning all the Pseudomonas HPPD mutants by simply replacing the truncated HPPD gene of this vector between the KpnI and BstEHl sites. It can also be used to clone the Synechocystis HPPD gene with a view to creating a transgenic plant.

B) Cloning Strategy

The sequence encoding Synechocystis HPPD is cloned into the pRD224 vector by replacing the sequence encoding the truncated Pseudomonas fluorescens HPPD. However, the Synechocystis HPPD sequence cannot be cloned directly between the KpnI and BstEII sites since the N-terminal sequences of the Synechocystis and Pseudomonas HPPD genes are very different. However, it is possible to clone between the BamHI site of the OTP and the BstEII site. In order to do this, it is necessary to recreate, from the 5' end, upstream of the HPPD sequence, the BamHI site followed by the part encoding OTP which is located downstream of BamHI.

The Synechocystis HPPD gene which is present in the vector pTRC99A is amplified by polymerization chain reaction (PCR) using primers A and B. The oligonucleotide A makes it possible to add the BamHI site upstream of the HPPD gene as well as a part of the OTP sequence between the BamHI site and the beginning of the gene. The oligonucleotide B makes it possible to add the BstEII site downstream of the gene. Primers A and B are depicted in SEQ ID NO 20 and 21:

5'NNNNNNNNNN GGATCCGGTG CATGGAATTC GAC-TATCTTC3'     oligonucleotide A

5'NNNNNNNNNN GGTCACCAGT ATTCATAATG TTAAT-TATG31'     oligonucleotide B

The amplification reaction is carried out at a hybridization temperature of 52° C. The PCR products are then separated on an agarose gel. The DNA band corresponding to the HPPD gene is cut out and purified.

The fragments which have thus been amplified are digested with BamHI at 37° C. for 1 hour and then with BstEII at 60° C. for 1 hour. This insert is then isolated on an agarose gel. The DNA band corresponding to the HPPD gene is cut out and purified.

This fragment is then cloned into the binary vector. The latter has previously been digested with BamHI and BstEII and then separated from the fragment corresponding to the truncated HPPD on an agarose gel. This vector is then purified in the same manner as the HPPD gene.

The ligation between the binary vector and the insert is carried out at 16° C. overnight using T4 DNA ligase. The ligation mixture is used to transform electrocompetent *E. coli* DH10B cells. The positive clones are selected on LB medium containing 50 mg/ml kanamycin. The presence of the insert of interest in the binary vector is checked on an agarose gel after carrying out a minipreparation and digesting the plasmid DNA with BamnHI and SacI at 37° C. for 1 hour. The recombinant vector is then used to transform electrocompetent *Agrobacterium tumefaciens* EHA105 cells. The selection is carried out on LB medium containing 50 mg/ml kanamycin. This recombinant vector is therefore carrying a T-DNA containing the gene for resistance to kanamycin, and a sequence encoding an OTP-Synechocystis HPPD unit under the control of the double histone promoter and a Nos terminator.

C) Transformation/regeneration of the PBD6 Tobacco Variety

The transformation is performed as described in Example 5 except that the selection is first of all carried out using 200 mg/ml kanamycin.

On the other hand, the young shoots which are obtained on kanamycin are excised and transferred individually onto a medium lacking hormones, in order to promote their rooting, and containing 2-cyano-3-cyclopropyl-1-(2-methylsulphonyl-4-trifluoromethylphenyl)propane-1,3-dione in order to select the transgenic plantlets which are tolerant to this herbicide. The medium is MS medium (SIGMA M-5519 4.4 g/l) containing 350 mg/l cefotaxime, 1% sucrose (w/v) and 0 or 8 ppm of 2-cyano-3-cyclopropyl-1-(2-methylsulphonyl-4-trifluoromethylphenyl)propane-1, 3-dione. The overproduction of HPPD in the transformed cells enables chlorophyllous plantlets to develop which are tolerant to 2-cyano-3-cyclopropyl-1-(2-methylsulphonyl-4-trifluoromethylphenyl)propane-1,3-dione, while the plantlets which are derived from untransformed cells, and which are sensitive to the herbicide, appear totally white.

After two weeks, the roots are sufficiently developed for the plantlets to be transferred into soil and cultivated in a greenhouse.

D) Results

In the case of each construct, approximately 40 shoots are regenerated from an average of 60 foliar discs. After 2 days of culture on a medium in the presence of 2-cyano-3-cyclopropyl-1-(2-methylsulphonyl-4-trifluoromethylphenyl)propane-1,3-dione, some plantlets begin to turn white. After 8 days of rooting, this whitening is sufficiently significant to be interpretable. At 8 ppm of 2-cyano-3-cyclopropyl-1-(2-methylsulphonyl-4-trifluoromethylphenyl)propane-1,3-dione, it is observed that only 40% of the plants harbouring the wild-type enzyme survive as against 72% for the plants harbouring the enzyme SyA318 and 88% for those harbouring the enzyme SyN318. The plants harbouring the mutated enzymes therefore exhibit a tolerance which is superior to that of the plants harbouring the wild-type enzyme.

After more than a month on 8ppm of 2-cyano-3-cyclopropyl-1-(2-methylsulphonyl-4-trifluoromethylphenyl)propane-1,3-dione, the number of green plantlets in the case of transformation with the wild-type HPPD is 0%, while in the case of SyN318 this percentage is 17% and in the case of the mutant SyA318 it is 19%.

In parallel, if the regeneration is carried out in the presence of concentrations of from 5 to 10 ppm of 2-cyano-1-[4-(methylsulphonyl)-2-trifluoromethylphenyl]-3-(1-methylcyclopropyl)propane-1,3-dione (EP496630)(a weaker inhibitor of the HPPDs), the three genes make it possible to obtain plants which are morphologically entirely in keeping.

These results appear to be in agreement with the results obtained in vitro by means of enzyme kinetics and it is possible to establish a correlation between the in vitro biochemical measurements and the results obtained in vivo.

This latter example confirms that there can be consistency between the screening in vitro (Example 1), the biochemical analysis (Example 7) and the tolerance of a plant.

What is claimed is:

1. An isolated nucleic acid which encodes an enzymatically-active, mutated HPPD, which HPPD has been mutated in its C-terminal part to be less sensitive to HPPD inhibitors than the native, unmutated HPPD.

2. A nucleic acid according to claim 1, wherein a linking peptide is located between 5 and 15 amino acids upstream of Asp161, with reference to Pseudomonas HPPD (SEQ ID NO:31).

3. A nucleic acid according to claim 2, wherein the C-terminal part consists of the part between the linking peptide and the C-terminal end of the HPPD.

4. A nucleic acid according to claim 1, wherein mutation is an amino acid substitution.

5. The nucleic acid according to claim 4, wherein the substitution is effected on at least one amino acid of the C-terminal part which is common to several HPPD sequences.

6. The nucleic acid of claim 4, comprising one or more substitutions selected from the group consisting of Pro215Leu, Gly336Glu, Gly336Trp, Gly336Ile and Ala340Gly.

7. The nucleic acid of claim 4, wherein the substitution adds amino acids which exhibit greater steric hindrance than the amino acids being replaced.

8. The nucleic acid of claim 4, wherein the substituted amino acids are replaced with glutamine (Gln), glutamic acid (Glu), leucine (Leu), isoleucine (Ile) or tryptophan (Trp).

9. The nucleic acid according to claim 1, wherein the mutation is carried out on the C-terminal part between the positions corresponding to positions 290 and 350 of the Pseudomonas sequence (SEQ ID NO:31).

10. The nucleic acid according to claim 9, wherein the mutation is a substitution of an amino acid at one of positions 298, 332, 333, 334, 336 or 340.

11. The nucleic acid of claim 9, wherein the mutation is an amino acid substitution at Pro215, Gly298, Gly332, Phe333, Gly334, Gly336 or Ala340.

12. The nucleic acid of claim 11, wherein the mutation is at Pro215, Gly336 or Ala340.

13. A nucleic acid of claim 1, wherein the HPPD contains, in its C-terminal part, the following peptide sequence:

- Gly - Phe - Xaa - Yaa- Xab - Asn - Phe - Yab - Yac - Leu - Phe - in which Xaa and Xab, independently of each other represent glycine (Gly) or an amino acid which exhibits a hindrance which is greater than that of glycine, with it being understood that if either Xaa or Xab represents Gly, the other amino acid is then different from Gly, and wherein Yaa represents Ala, Lys or Glu, Yab represents Lys, Ser, Arg or Asn, and Yac represents Ala, Ser, Glu or Gln.

14. A nucleic acid sequence of claim 13, wherein at least one of Xaa and Xab represents Leu, Glu, Trp or Ile.

15. A nucleic acid sequence of claim 14, wherein Xab represents Glu, Trp or Ile.

16. A nucleic acid sequence of claim 15, wherein Xab represents Trp.

17. A chimeric gene which comprises the nucleic acid of claim 1 and regulatory elements allowing its expression in a host, wherein the host is plant, a plant cell, or a bacteria.

18. The chimeric gene of claim 17, wherein the host is plant.

19. The chimeric gene of claim 18, further comprising sequence encoding a transit peptide.

20. A plant cell which contains the chimeric gene of claim 19.

21. A plant transformation vector comprising the chimeric gene of claim 17.

22. A plant cell which contains the chimeric gene of claim 18.

23. A plant which contains the chimeric gene of claim 19, which is tolerant to HPPD herbicides.

24. A seed of a plant as claimed in claim 23.

25. A plant which contains the chimeric gene of claim 17, which is tolerant to HPPD herbicides.

26. A seed of a plant as claimed in claim 25.

27. A method which comprises growing the plant of claim 25 in a field, and applying an HPPD herbicide to the field.

28. A method which comprises growing the plant of claim 23 in a field, and applying an HPPD herbicide to the field.

29. A plant which contains the nucleic acid of claim 1 and which is tolerant to HPPD herbicides.

* * * * *

SEQUENCE LISTING

```
<160> NUMBER OF SEQ ID NOS: 31

<210> SEQ ID NO: 1
<211> LENGTH: 33
<212> TYPE: DNA
<213> ORGANISM: Plant

<400> SEQUENCE: 1
gaagttgccc tcgccccacc catcgtcgcc ctt                                33

<210> SEQ ID NO: 2
<211> LENGTH: 33
<212> TYPE: DNA
<213> ORGANISM: Plant

<400> SEQUENCE: 2
gaagttgccc tcgccrakcc catcgtcgcc ctt                                33

<210> SEQ ID NO: 3
<211> LENGTH: 33
<212> TYPE: DNA
<213> ORGANISM: Plant

<400> SEQUENCE: 3
cttgaagttg ccctcccaaa acccatcgtc gcc                                33

<210> SEQ ID NO: 4
<211> LENGTH: 33
<212> TYPE: DNA
<213> ORGANISM: Plant

<400> SEQUENCE: 4
cttgaagttg ccctcgtcaa acccatcgtc gcc                                33

<210> SEQ ID NO: 5
<211> LENGTH: 33
<212> TYPE: DNA
<213> ORGANISM: Plant

<400> SEQUENCE: 5
cttgaagttg ccctcgctaa acccatcgtc gcc                                33

<210> SEQ ID NO: 6
<211> LENGTH: 33
<212> TYPE: DNA
<213> ORGANISM: Plant
```

```
<400> SEQUENCE: 6
cttgaagttg ccctcrakaa acccatcgtc gcc                                    33

<210> SEQ ID NO: 7
<211> LENGTH: 33
<212> TYPE: DNA
<213> ORGANISM: Plant

<400> SEQUENCE: 7
cagcgccttg aagttgtcct cgccaaaccc atc                                    33

<210> SEQ ID NO: 8
<211> LENGTH: 33
<212> TYPE: DNA
<213> ORGANISM: Plant

<400> SEQUENCE: 8
cagcgccttg aagttytcct cgccaaaccc atc                                    33

<210> SEQ ID NO: 9
<211> LENGTH: 33
<212> TYPE: DNA
<213> ORGANISM: Plant

<400> SEQUENCE: 9
cagcgccttg aagttccact cgccaaaccc atc                                    33

<210> SEQ ID NO: 10
<211> LENGTH: 32
<212> TYPE: DNA
<213> ORGANISM: Plant

<400> SEQUENCE: 10
cagcgccttg aagttdactc gccaaaccca tc                                     32

<210> SEQ ID NO: 11
<211> LENGTH: 32
<212> TYPE: DNA
<213> ORGANISM: Plant
<220> FEATURE:
<221> NAME/KEY: unsure
<222> LOCATION: (12,14)..(18,20)
<223> OTHER INFORMATION: any nucleic acid: a, c, g, or t

<400> SEQUENCE: 11
cgcttgaagt tnnnctcnnn aaacccatcg tc                                     32

<210> SEQ ID NO: 12
<211> LENGTH: 33
<212> TYPE: DNA
<213> ORGANISM: Plant

<400> SEQUENCE: 12
gaacagcgcc ttgaarakgc cctcgccaaa ccc                                    33

<210> SEQ ID NO: 13
<211> LENGTH: 33
<212> TYPE: DNA
<213> ORGANISM: Plant

<400> SEQUENCE: 13
gccttccacg gaagattcgt ccagcaggat acc                                    33
```

```
<210> SEQ ID NO: 14
<211> LENGTH: 23
<212> TYPE: DNA
<213> ORGANISM: Plant

<400> SEQUENCE: 14
tcgagagaga ggtgaccgag aga                                              23

<210> SEQ ID NO: 15
<211> LENGTH: 23
<212> TYPE: DNA
<213> ORGANISM: Plant

<400> SEQUENCE: 15
tcgatctctc ggtcacctct ctc                                              23

<210> SEQ ID NO: 16
<211> LENGTH: 21
<212> TYPE: DNA
<213> ORGANISM: Plant

<400> SEQUENCE: 16
attatggaat tcgactatct t                                                21

<210> SEQ ID NO: 17
<211> LENGTH: 23
<212> TYPE: DNA
<213> ORGANISM: Plant

<400> SEQUENCE: 17
cagtattcat aatgttaatt atg                                              23

<210> SEQ ID NO: 18
<211> LENGTH: 34
<212> TYPE: DNA
<213> ORGANISM: Plant

<400> SEQUENCE: 18
cgggcaaaag gatttarcca aggaaacttt caag                                  34

<210> SEQ ID NO: 19
<211> LENGTH: 34
<212> TYPE: DNA
<213> ORGANISM: Plant
<220> FEATURE:
<221> NAME/KEY: unsure
<222> LOCATION: (18)
<223> OTHER INFORMATION: any nucleic acid: a, c, g or t

<400> SEQUENCE: 19
cgggcaaaag gatttscnca aggaaacttt caag                                  34

<210> SEQ ID NO: 20
<211> LENGTH: 40
<212> TYPE: DNA
<213> ORGANISM: Plant
<220> FEATURE:
<221> NAME/KEY: unsure
<222> LOCATION: (1)..(10)
<223> OTHER INFORMATION: any nucleic acid: a, c, g or t

<400> SEQUENCE: 20
nnnnnnnnnn ggatccggtg catggaattc gactatcttc                            40
```

-continued

```
<210> SEQ ID NO: 21
<211> LENGTH: 39
<212> TYPE: DNA
<213> ORGANISM: Plant
<220> FEATURE:
<221> NAME/KEY: unsure
<222> LOCATION: (1)..(10)
<223> OTHER INFORMATION: any nucleic acid: a, c, g or t

<400> SEQUENCE: 21
nnnnnnnnnn ggtcaccagt attcataatg ttaattatg                              39

<210> SEQ ID NO: 22
<211> LENGTH: 46
<212> TYPE: DNA
<213> ORGANISM: Plant

<400> SEQUENCE: 22
ttcgatggac tcgaacagcg ccttgaagtt gccctcgcca aaccca                      46

<210> SEQ ID NO: 23
<211> LENGTH: 393
<212> TYPE: PRT
<213> ORGANISM: Mus musculus

<400> SEQUENCE: 23
```

Met Thr Thr Tyr Asn Asn Lys Gly Pro Lys Pro Glu Arg Gly Arg Phe
1               5                   10                  15

Leu His Phe His Ser Val Thr Phe Trp Val Gly Asn Ala Lys Gln Ala
            20                  25                  30

Ala Ser Phe Tyr Cys Asn Lys Met Gly Phe Glu Pro Leu Ala Tyr Arg
        35                  40                  45

Gly Leu Glu Thr Gly Ser Arg Glu Val Val Ser His Val Ile Lys Arg
    50                  55                  60

Gly Lys Ile Val Phe Val Leu Cys Ser Ala Leu Asn Pro Trp Asn Lys
65                  70                  75                  80

Glu Met Gly Asp His Leu Val Lys His Gly Asp Gly Val Lys Asp Ile
                85                  90                  95

Ala Phe Glu Val Glu Asp Cys Asp His Ile Val Gln Lys Ala Arg Glu
            100                 105                 110

Arg Gly Ala Lys Ile Val Arg Glu Pro Trp Val Glu Gln Asp Lys Phe
        115                 120                 125

Gly Lys Val Lys Phe Ala Val Leu Gln Thr Tyr Gly Asp Thr Thr His
    130                 135                 140

Thr Leu Val Glu Lys Ile Asn Tyr Thr Gly Arg Phe Leu Pro Gly Phe
145                 150                 155                 160

Glu Ala Pro Thr Tyr Lys Asp Thr Leu Leu Pro Lys Leu Pro Arg Cys
                165                 170                 175

Asn Leu Glu Ile Ile Asp His Ile Val Gly Asn Gln Pro Asp Gln Glu
            180                 185                 190

Met Gln Ser Ala Ser Glu Trp Tyr Leu Lys Asn Leu Gln Phe His Arg
        195                 200                 205

Phe Trp Ser Val Asp Asp Thr Gln Val His Thr Glu Tyr Ser Ser Leu
    210                 215                 220

Arg Ser Ile Val Val Thr Asn Tyr Glu Glu Ser Ile Lys Met Pro Ile
225                 230                 235                 240

Asn Glu Pro Ala Pro Gly Arg Lys Lys Ser Gln Ile Gln Glu Tyr Val
                245                 250                 255

-continued

```
Asp Tyr Asn Gly Gly Ala Gly Val Gln His Ile Ala Leu Lys Thr Glu
            260                 265                 270

Asp Ile Ile Thr Ala Ile Arg His Leu Arg Glu Arg Gly Thr Glu Phe
        275                 280                 285

Leu Ala Ala Pro Ser Ser Tyr Tyr Lys Leu Leu Arg Glu Asn Leu Lys
    290                 295                 300

Ser Ala Lys Ile Gln Val Lys Glu Ser Met Asp Val Leu Glu Glu Leu
305                 310                 315                 320

His Ile Leu Val Asp Tyr Asp Glu Lys Gly Tyr Leu Leu Gln Ile Phe
                325                 330                 335

Thr Lys Pro Met Gln Asp Arg Pro Thr Leu Phe Leu Glu Val Ile Gln
            340                 345                 350

Arg His Asn His Gln Gly Phe Gly Ala Gly Asn Phe Asn Ser Leu Phe
        355                 360                 365

Lys Ala Phe Glu Glu Glu Gln Ala Leu Arg Gly Asn Leu Thr Asp Leu
    370                 375                 380

Glu Pro Asn Gly Val Arg Ser Gly Met
385                 390
```

<210> SEQ ID NO: 24
<211> LENGTH: 399
<212> TYPE: PRT
<213> ORGANISM: Coccidioides immitis

<400> SEQUENCE: 24

```
Met Ala Pro Ala Ala Asp Ser Pro Thr Leu Gln Pro Ala Gln Pro Ser
  1               5                  10                  15

Asp Leu Asn Gln Tyr Arg Gly Tyr Asp His Val His Trp Tyr Val Gly
             20                  25                  30

Asn Ala Lys Gln Ala Ala Thr Tyr Tyr Val Thr Arg Met Gly Phe Glu
         35                  40                  45

Arg Val Ala Tyr Arg Gly Leu Glu Thr Gly Ser Lys Ala Val Ala Ser
     50                  55                  60

His Val Val Arg Asn Gly Asn Ile Thr Phe Ile Leu Thr Ser Pro Leu
 65                  70                  75                  80

Arg Ser Val Glu Gln Ala Ser Arg Phe Pro Glu Asp Glu Ala Leu Leu
                 85                  90                  95

Lys Glu Ile His Ala His Leu Glu Arg His Gly Asp Gly Val Lys Asp
            100                 105                 110

Val Ala Phe Glu Val Asp Cys Val Glu Ser Val Phe Ser Ala Ala Val
        115                 120                 125

Arg Asn Gly Ala Glu Val Val Ser Asp Val Arg Thr Val Glu Asp Glu
    130                 135                 140

Asp Gly Gln Ile Lys Met Ala Thr Ile Arg Thr Tyr Gly Glu Thr Thr
145                 150                 155                 160

His Thr Leu Ile Glu Arg Ser Gly Tyr Arg Gly Gly Phe Met Pro Gly
                165                 170                 175

Tyr Arg Met Glu Ser Asn Ala Asp Ala Thr Ser Lys Phe Leu Pro Lys
            180                 185                 190

Val Val Leu Glu Arg Ile Asp His Cys Val Gly Asn Gln Asp Trp Asp
        195                 200                 205

Glu Met Glu Arg Val Cys Asp Tyr Tyr Glu Lys Ile Leu Gly Phe His
    210                 215                 220

Arg Phe Trp Ser Val Asp Asp Lys Asp Ile Cys Thr Glu Phe Ser Ala
225                 230                 235                 240
```

-continued

```
Leu Lys Ser Ile Val Met Ala Ser Pro Asn Asp Ile Val Lys Met Pro
                245                 250                 255

Ile Asn Glu Pro Ala Lys Gly Lys Lys Gln Ser Gln Ile Glu Glu Tyr
            260                 265                 270

Val Asp Phe Tyr Asn Gly Ala Gly Val Gln His Ile Ala Leu Arg Thr
        275                 280                 285

Asn Asn Ile Ile Asp Ala Ile Thr Asn Leu Lys Ala Arg Gly Thr Glu
    290                 295                 300

Phe Ile Lys Val Pro Glu Thr Tyr Tyr Glu Asp Met Lys Ile Arg Leu
305                 310                 315                 320

Lys Arg Gln Gly Leu Val Leu Asp Glu Asp Phe Glu Thr Leu Lys Ser
                325                 330                 335

Leu Asp Ile Leu Ile Asp Phe Asp Glu Asn Gly Tyr Leu Leu Gln Leu
            340                 345                 350

Phe Thr Lys His Leu Met Asp Arg Pro Thr Val Phe Ile Glu Ile Ile
        355                 360                 365

Gln Arg Asn Asn Phe Ser Gly Phe Gly Ala Gly Asn Phe Arg Ala Leu
    370                 375                 380

Phe Glu Ala Ile Glu Arg Glu Gln Ala Leu Arg Gly Thr Leu Ile
385                 390                 395

<210> SEQ ID NO: 25
<211> LENGTH: 419
<212> TYPE: PRT
<213> ORGANISM: Mycosphaerella graminicola

<400> SEQUENCE: 25

Met Ala Pro Gly Ala Leu Leu Val Thr Ser Gln Asn Gly Arg Thr Ser
1               5                   10                  15

Pro Leu Tyr Asp Ser Asp Gly Tyr Val Pro Ala Pro Ala Ala Leu Val
            20                  25                  30

Val Gly Gly Glu Val Asn Tyr Arg Gly Tyr His His Ala Glu Trp Trp
        35                  40                  45

Val Gly Asn Ala Lys Gln Val Ala Gln Phe Tyr Ile Thr Arg Met Gly
    50                  55                  60

Phe Glu Pro Val Ala His Lys Gly Leu Glu Thr Gly Ser Arg Phe Phe
65                  70                  75                  80

Ala Ser His Val Val Gln Asn Asn Gly Val Arg Phe Val Phe Thr Ser
                85                  90                  95

Pro Val Arg Ser Ser Ala Arg Gln Thr Leu Lys Ala Ala Pro Leu Ala
            100                 105                 110

Asp Gln Ala Arg Leu Asp Glu Met Tyr Asp His Leu Asp Lys His Gly
        115                 120                 125

Asp Gly Val Lys Asp Val Ala Phe Glu Val Asp Val Leu Ala Val
    130                 135                 140

Tyr Glu Asn Ala Val Ala Asn Gly Ala Glu Ser Val Ser Ser Pro His
145                 150                 155                 160

Thr Asp Ser Cys Asp Glu Gly Asp Val Ile Ser Ala Ala Ile Lys Thr
                165                 170                 175

Tyr Gly Asp Thr Thr His Thr Phe Ile Gln Arg Thr Thr Tyr Thr Gly
            180                 185                 190

Pro Phe Leu Pro Gly Tyr Arg Ser Cys Thr Thr Val Asp Ser Ala Asn
        195                 200                 205

Lys Phe Leu Pro Pro Val Asn Leu Glu Ala Ile Asp His Cys Val Gly
    210                 215                 220
```

```
Asn Gln Asp Trp Asp Glu Met Ser Asp Ala Cys Asp Phe Tyr Glu Arg
225                 230                 235                 240

Cys Leu Gly Phe His Arg Phe Trp Ser Val Asp Asp Lys Asp Ile Cys
            245                 250                 255

Thr Glu Phe Ser Ala Leu Lys Ser Ile Val Met Ser Ser Pro Asn Gln
            260                 265                 270

Val Val Lys Met Pro Ile Asn Glu Pro Ala His Gly Lys Lys Lys Ser
            275                 280                 285

Gln Ile Glu Glu Tyr Val Asp Phe Tyr Asn Gly Pro Gly Val Gln His
            290                 295                 300

Ile Ala Leu Arg Thr Pro Asn Ile Ile Glu Ala Val Ser Asn Leu Arg
305                 310                 315                 320

Ser Arg Gly Val Glu Phe Ile Ser Val Pro Asp Thr Tyr Tyr Glu Asn
                325                 330                 335

Met Arg Leu Arg Leu Lys Ala Ala Gly Met Lys Leu Glu Glu Ser Phe
            340                 345                 350

Asp Ile Ile Gln Lys Leu Asn Ile Leu Ile Asp Phe Asp Glu Gly Gly
                355                 360                 365

Tyr Leu Leu Gln Leu Phe Thr Lys Pro Leu Met Asp Arg Pro Thr Val
            370                 375                 380

Phe Ile Glu Ile Ile Gln Arg Asn Asn Phe Asp Gly Phe Gly Ala Gly
385                 390                 395                 400

Asn Phe Lys Ser Leu Phe Glu Ala Ile Glu Arg Glu Gln Asp Leu Arg
                405                 410                 415

Gly Asn Leu

<210> SEQ ID NO: 26
<211> LENGTH: 434
<212> TYPE: PRT
<213> ORGANISM: Hordeum vulgare

<400> SEQUENCE: 26

Met Pro Pro Thr Pro Thr Thr Pro Ala Ala Thr Gly Ala Ala Ala Ala
1               5                   10                  15

Val Thr Pro Glu His Ala Arg Pro His Arg Met Val Arg Phe Asn Pro
                20                  25                  30

Arg Ser Asp Arg Phe His Thr Leu Ser Phe His His Val Glu Phe Trp
            35                  40                  45

Cys Ala Asp Ala Ala Ser Ala Ala Gly Arg Phe Ala Phe Ala Leu Gly
        50                  55                  60

Ala Pro Leu Ala Ala Arg Ser Asp Leu Ser Thr Gly Asn Ser Ala His
65                  70                  75                  80

Ala Ser Gln Leu Leu Arg Ser Gly Ser Leu Ala Phe Leu Phe Thr Ala
                85                  90                  95

Pro Tyr Ala Asn Gly Cys Asp Ala Ala Thr Ala Ser Leu Pro Ser Phe
                100                 105                 110

Ser Ala Asp Ala Ala Arg Arg Phe Ser Ala Asp His Gly Ile Ala Val
            115                 120                 125

Arg Ser Val Ala Leu Arg Val Ala Asp Ala Ala Glu Ala Phe Arg Ala
130                 135                 140

Ser Arg Arg Gly Ala Arg Pro Ala Phe Ala Pro Val Asp Leu Gly
145                 150                 155                 160

Arg Gly Phe Ala Phe Ala Glu Val Glu Leu Tyr Gly Asp Val Val Leu
                165                 170                 175
```

-continued

```
Arg Phe Val Ser His Pro Asp Gly Thr Asp Val Pro Phe Leu Pro Gly
            180                 185                 190

Phe Glu Gly Val Thr Asn Pro Asp Ala Val Asp Tyr Gly Leu Thr Arg
            195                 200                 205

Phe Asp His Val Val Gly Asn Val Pro Glu Leu Ala Pro Ala Ala Ala
            210                 215                 220

Tyr Ile Ala Gly Phe Thr Gly Phe His Glu Phe Ala Glu Phe Thr Ala
225                 230                 235                 240

Glu Asp Val Gly Thr Thr Glu Ser Gly Leu Asn Ser Val Val Leu Ala
            245                 250                 255

Asn Asn Ser Glu Gly Val Leu Leu Pro Leu Asn Glu Pro Val His Gly
            260                 265                 270

Thr Lys Arg Arg Ser Gln Ile Gln Thr Phe Leu Glu His Gly Gly
            275                 280                 285

Pro Gly Val Gln His Ile Ala Val Ala Ser Ser Asp Val Leu Arg Thr
            290                 295                 300

Leu Arg Lys Met Arg Ala Arg Ser Ala Met Gly Gly Phe Asp Phe Leu
305                 310                 315                 320

Pro Pro Pro Leu Pro Lys Tyr Tyr Glu Gly Val Arg Arg Leu Ala Gly
            325                 330                 335

Asp Val Leu Ser Glu Ala Gln Ile Lys Glu Cys Gln Glu Leu Gly Val
            340                 345                 350

Leu Val Asp Arg Asp Asp Gln Gly Val Leu Leu Gln Ile Phe Thr Lys
            355                 360                 365

Pro Val Gly Asp Arg Pro Thr Leu Phe Leu Glu Met Ile Gln Arg Ile
            370                 375                 380

Gly Cys Met Glu Lys Asp Glu Arg Gly Glu Glu Tyr Gln Lys Gly Gly
385                 390                 395                 400

Cys Gly Gly Phe Gly Lys Gly Asn Phe Ser Glu Leu Phe Lys Ser Ile
            405                 410                 415

Glu Asp Tyr Glu Lys Ser Leu Glu Ala Lys Gln Ser Ala Ala Val Gln
            420                 425                 430

Gly Ser

<210> SEQ ID NO: 27
<211> LENGTH: 444
<212> TYPE: PRT
<213> ORGANISM: Zea mays

<400> SEQUENCE: 27

Met Pro Pro Thr Pro Thr Ala Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe His Thr Leu Ala Phe
        35                  40                  45

His His Val Glu Leu Trp Cys Ala Asp Ala Ala Ser Ala Ala Gly Arg
    50                  55                  60

Phe Ser Phe Gly Leu Gly Ala Pro Leu Ala Ala Arg Ser Asp Leu Ser
65                  70                  75                  80

Thr Gly Asn Ser Ala His Ala Ser Leu Leu Leu Arg Ser Gly Ser Leu
            85                  90                  95

Ser Phe Leu Phe Thr Ala Pro Tyr Ala His Gly Ala Asp Ala Ala Thr
            100                 105                 110
```

-continued

```
Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
210                 215                 220

Glu Leu Ala Pro Ala Ala Tyr Phe Ala Gly Phe Thr Gly Phe His
225                 230                 235                 240

Glu Phe Ala Glu Phe Thr Thr Glu Asp Val Gly Thr Ala Glu Ser Gly
                245                 250                 255

Leu Asn Ser Met Val Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Met Ala Leu Ala
290                 295                 300

Ser Asp Asp Val Leu Arg Thr Leu Arg Glu Met Gln Ala Arg Ser Ala
305                 310                 315                 320

Met Gly Gly Phe Glu Phe Met Ala Pro Pro Thr Ser Asp Tyr Tyr Asp
                325                 330                 335

Gly Val Arg Arg Arg Ala Gly Asp Val Leu Thr Glu Ala Gln Ile Lys
            340                 345                 350

Glu Cys Gln Glu Leu Gly Val Leu Val Asp Arg Asp Gln Gly Val
        355                 360                 365

Leu Leu Gln Ile Phe Thr Lys Pro Val Gly Asp Arg Pro Thr Leu Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Ser Gln Leu Phe Lys Ser Ile Glu Asp Tyr Glu Lys Ser Leu Glu Ala
            420                 425                 430

Lys Gln Ala Ala Ala Ala Ala Ala Gln Gly Ser
        435                 440

<210> SEQ ID NO: 28
<211> LENGTH: 445
<212> TYPE: PRT
<213> ORGANISM: Arabidopsis thaliana

<400> SEQUENCE: 28

Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
            20                  25                  30

Val Arg Lys Asn Pro Lys Ser Asp Lys Phe Lys Val Lys Arg Phe His
        35                  40                  45
```

-continued

```
His Ile Glu Phe Trp Cys Gly Asp Ala Thr Asn Val Ala Arg Arg Phe
    50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
                85                  90                  95

Phe Leu Phe Thr Ala Pro Tyr Ser Pro Ser Leu Ser Ala Gly Glu Ile
            100                 105                 110

Lys Pro Thr Thr Thr Ala Ser Ile Pro Ser Phe Asp His Gly Ser Cys
        115                 120                 125

Arg Ser Phe Phe Ser Ser His Gly Leu Gly Val Arg Ala Val Ala Ile
    130                 135                 140

Glu Val Glu Asp Ala Glu Ser Ala Phe Ser Ile Ser Val Ala Asn Gly
145                 150                 155                 160

Ala Ile Pro Ser Ser Pro Pro Ile Val Leu Asn Glu Ala Val Thr Ile
                165                 170                 175

Ala Glu Val Lys Leu Tyr Gly Asp Val Val Leu Arg Tyr Val Ser Tyr
            180                 185                 190

Lys Ala Glu Asp Thr Glu Lys Ser Glu Phe Leu Pro Gly Phe Glu Arg
        195                 200                 205

Val Glu Asp Ala Ser Ser Phe Pro Leu Asp Tyr Gly Ile Arg Arg Leu
    210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
                245                 250                 255

Asp Val Gly Thr Ala Glu Ser Gly Leu Asn Ser Ala Val Leu Ala Ser
            260                 265                 270

Asn Asp Glu Met Val Leu Leu Pro Ile Asn Glu Pro Val His Gly Thr
        275                 280                 285

Lys Arg Lys Ser Gln Ile Gln Thr Tyr Leu Glu His Asn Glu Gly Ala
    290                 295                 300

Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
                325                 330                 335

Ser Pro Pro Pro Thr Tyr Tyr Gln Asn Leu Lys Lys Arg Val Gly Asp
            340                 345                 350

Val Leu Ser Asp Asp Gln Ile Lys Glu Cys Glu Glu Leu Gly Ile Leu
        355                 360                 365

Val Asp Arg Asp Asp Gln Gly Thr Leu Leu Gln Ile Phe Thr Lys Pro
    370                 375                 380

Leu Gly Asp Arg Pro Thr Ile Phe Ile Glu Ile Ile Gln Arg Val Gly
385                 390                 395                 400

Cys Met Met Lys Asp Glu Glu Gly Lys Ala Tyr Gln Ser Gly Gly Cys
                405                 410                 415

Gly Gly Phe Gly Lys Gly Asn Phe Ser Glu Leu Phe Lys Ser Ile Glu
            420                 425                 430

Glu Tyr Glu Lys Thr Leu Glu Ala Lys Gln Leu Val Gly
        435                 440                 445
```

```
<210> SEQ ID NO: 29
<211> LENGTH: 442
<212> TYPE: PRT
<213> ORGANISM: Daucus carota

<400> SEQUENCE: 29

Met Gly Lys Lys Gln Ser Glu Ala Glu Ile Leu Ser Ser Asn Ser Ser
 1               5                  10                  15

Asn Thr Ser Pro Ala Thr Phe Lys Leu Val Gly Phe Asn Asn Phe Val
                20                  25                  30

Arg Ala Asn Pro Lys Ser Asp His Phe Ala Val Lys Arg Phe His His
            35                  40                  45

Ile Glu Phe Trp Cys Gly Asp Ala Thr Asn Thr Ser Arg Arg Phe Ser
 50                  55                  60

Trp Gly Leu Gly Met Pro Leu Val Ala Lys Ser Asp Leu Ser Thr Gly
 65                  70                  75                  80

Asn Ser Val His Ala Ser Tyr Leu Val Arg Ser Ala Asn Leu Ser Phe
                85                  90                  95

Val Phe Thr Ala Pro Tyr Ser Pro Ser Thr Thr Thr Ser Ser Gly Ser
                100                 105                 110

Ala Ala Ile Pro Ser Phe Ser Ala Ser Gly Phe His Ser Phe Ala Ala
            115                 120                 125

Lys His Gly Leu Ala Val Arg Ala Ile Ala Leu Glu Val Ala Asp Val
130                 135                 140

Ala Ala Ala Phe Glu Ala Ser Val Ala Arg Gly Ala Arg Pro Ala Ser
145                 150                 155                 160

Ala Pro Val Glu Leu Asp Asp Gln Ala Trp Leu Ala Glu Val Glu Leu
                165                 170                 175

Tyr Gly Asp Val Val Leu Arg Phe Val Ser Phe Gly Arg Glu Glu Gly
                180                 185                 190

Leu Phe Leu Pro Gly Phe Glu Ala Val Glu Gly Thr Ala Ser Phe Pro
            195                 200                 205

Asp Leu Asp Tyr Gly Ile Arg Arg Leu Asp His Ala Val Gly Asn Val
210                 215                 220

Thr Glu Leu Gly Pro Val Val Glu Tyr Ile Lys Gly Phe Thr Gly Phe
225                 230                 235                 240

His Glu Phe Ala Glu Phe Thr Ala Glu Asp Val Gly Thr Leu Glu Ser
                245                 250                 255

Gly Leu Asn Ser Val Val Leu Ala Asn Asn Glu Glu Met Val Leu Leu
                260                 265                 270

Pro Leu Asn Glu Pro Val Tyr Gly Thr Lys Arg Lys Ser Gln Ile Gln
            275                 280                 285

Thr Tyr Leu Glu His Asn Glu Gly Ala Gly Val Gln His Leu Ala Leu
290                 295                 300

Val Ser Glu Asp Ile Phe Arg Thr Leu Arg Glu Met Arg Lys Arg Ser
305                 310                 315                 320

Cys Leu Gly Gly Phe Glu Phe Met Pro Ser Pro Pro Thr Tyr Tyr
                325                 330                 335

Lys Asn Leu Lys Asn Arg Val Gly Asp Val Leu Ser Asp Glu Gln Ile
            340                 345                 350

Lys Glu Cys Glu Asp Leu Gly Ile Leu Val Asp Arg Asp Asp Gln Gly
355                 360                 365

Thr Leu Leu Gln Ile Phe Thr Lys Pro Val Gly Asp Arg Pro Thr Leu
370                 375                 380
```

```
Phe Ile Glu Ile Ile Gln Arg Val Gly Cys Met Leu Lys Asp Asp Ala
385                 390                 395                 400

Gly Gln Met Tyr Gln Lys Gly Gly Cys Gly Gly Phe Gly Lys Gly Asn
            405                 410                 415

Phe Ser Glu Leu Phe Lys Ser Ile Glu Glu Tyr Glu Lys Thr Leu Glu
            420                 425                 430

Ala Lys Gln Ile Thr Gly Ser Ala Ala Ala
            435                 440

<210> SEQ ID NO: 30
<211> LENGTH: 380
<212> TYPE: PRT
<213> ORGANISM: Streptomyces avermitilis

<400> SEQUENCE: 30

Met Thr Gln Thr Thr His His Thr Pro Asp Thr Ala Arg Gln Ala Asp
 1               5                  10                  15

Pro Phe Pro Val Lys Gly Met Asp Ala Val Phe Ala Val Gly Asn
                20                  25                  30

Ala Lys Gln Ala Ala His Tyr Ser Thr Ala Phe Gly Met Gln Leu Val
            35                  40                  45

Ala Tyr Ser Gly Pro Glu Asn Gly Ser Arg Glu Thr Ala Ser Tyr Val
    50                  55                  60

Leu Thr Asn Gly Ser Ala Arg Phe Val Leu Thr Ser Val Ile Lys Pro
65                  70                  75                  80

Ala Thr Pro Trp Gly His Phe Leu Ala Asp His Val Ala Glu His Gly
                85                  90                  95

Asp Gly Val Val Asp Leu Ala Ile Glu Val Pro Asp Ala Arg Ala Ala
                100                 105                 110

His Ala Tyr Ala Ile Glu His Gly Ala Arg Ser Val Ala Glu Pro Tyr
            115                 120                 125

Glu Leu Lys Asp Glu His Gly Thr Val Val Leu Ala Ala Ile Ala Thr
            130                 135                 140

Tyr Gly Lys Thr Arg His Thr Leu Val Asp Arg Thr Gly Tyr Asp Gly
145                 150                 155                 160

Pro Tyr Leu Pro Gly Tyr Val Ala Ala Pro Ile Val Glu Pro Pro
                165                 170                 175

Ala His Arg Thr Phe Gln Ala Ile Asp His Cys Val Gly Asn Val Glu
            180                 185                 190

Leu Gly Arg Met Asn Glu Trp Val Gly Phe Tyr Asn Lys Val Met Gly
        195                 200                 205

Phe Thr Asn Met Lys Glu Phe Val Gly Asp Ile Ala Thr Glu Tyr
        210                 215                 220

Ser Ala Leu Met Ser Lys Val Val Ala Asp Gly Thr Leu Lys Val Lys
225                 230                 235                 240

Phe Pro Ile Asn Glu Pro Ala Leu Ala Lys Lys Lys Ser Gln Ile Asp
                245                 250                 255

Glu Tyr Leu Glu Phe Tyr Gly Gly Ala Gly Val Gln His Ile Ala Leu
            260                 265                 270

Asn Thr Gly Asp Ile Val Glu Thr Val Arg Thr Met Arg Ala Ala Gly
        275                 280                 285

Val Gln Phe Leu Asp Thr Pro Asp Ser Tyr Tyr Asp Thr Leu Gly Glu
    290                 295                 300

Trp Val Gly Asp Thr Arg Val Pro Val Asp Thr Leu Arg Glu Leu Lys
305                 310                 315                 320
```

Ile Leu Ala Asp Arg Asp Glu Asp Gly Tyr Leu Leu Gln Ile Phe Thr
                325                 330                 335

Lys Pro Val Gln Asp Arg Pro Thr Val Phe Phe Glu Ile Ile Glu Arg
                340                 345                 350

His Gly Ser Met Gly Phe Gly Lys Gly Asn Phe Lys Ala Leu Phe Glu
                355                 360                 365

Ala Ile Glu Arg Glu Gln Glu Lys Arg Gly Asn Leu
                370                 375                 380

<210> SEQ ID NO: 31
<211> LENGTH: 358
<212> TYPE: PRT
<213> ORGANISM: Pseudomonas fluorescens

<400> SEQUENCE: 31

Met Ala Asp Leu Tyr Glu Asn Pro Met Gly Leu Met Gly Phe Glu Phe
  1               5                  10                  15

Ile Glu Phe Ala Ser Pro Thr Pro Gly Thr Leu Glu Pro Ile Phe Glu
                 20                  25                  30

Ile Met Gly Phe Thr Lys Val Ala Thr His Arg Ser Lys Asn Val His
             35                  40                  45

Leu Tyr Arg Gln Gly Glu Ile Asn Leu Ile Leu Asn Asn Glu Pro Asn
         50                  55                  60

Ser Ile Ala Ser Tyr Phe Ala Ala Glu His Gly Pro Ser Val Cys Gly
 65                  70                  75                  80

Met Ala Phe Arg Val Lys Asp Ser Gln Lys Ala Tyr Asn Arg Ala Leu
                 85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

```
                                              -continued
Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
                340                 345                 350

Gly Val Leu Thr Ala Asp
                355
```